US007981656B2

(12) United States Patent
Sanders et al.

(10) Patent No.: US 7,981,656 B2
(45) Date of Patent: Jul. 19, 2011

(54) PSEUDOTYPED RETROVIRUS WITH MODIFIED EBOLA GLYCOPROTEIN

(75) Inventors: David A. Sanders, West Lafayette, IN (US); Scott A. Jeffers, Aurora, CO (US); Anthony Sanchez, Lilburn, GA (US)

(73) Assignees: Purdue Research Foundation, West Lafayette, IN (US); Centers for Disease Control and Prevention, Atlanta, GA (US)

( * ) Notice: Subject to any disclaimer, the term of this patent is extended or adjusted under 35 U.S.C. 154(b) by 1264 days.

(21) Appl. No.: 10/516,578

(22) PCT Filed: Jun. 4, 2003

(86) PCT No.: PCT/US03/17577
§ 371 (c)(1),
(2), (4) Date: Nov. 16, 2005

(87) PCT Pub. No.: WO03/102219
PCT Pub. Date: Dec. 11, 2003

(65) Prior Publication Data
US 2006/0093590 A1      May 4, 2006

Related U.S. Application Data

(60) Provisional application No. 60/386,064, filed on Jun. 4, 2002, provisional application No. 60/458,070, filed on Mar. 27, 2003.

(51) Int. Cl.
*C12N 7/00* (2006.01)
*C07H 21/02* (2006.01)

(52) U.S. Cl. .................... 435/235.1; 977/802; 977/803; 536/23.1

(58) Field of Classification Search ........................ None
See application file for complete search history.

(56) References Cited

U.S. PATENT DOCUMENTS

| | | | |
|---|---|---|---|
| 4,912,030 A | 3/1990 | Weiss et al. | |
| 5,185,440 A | 2/1993 | Davis et al. | |
| 5,278,056 A | 1/1994 | Bank et al. | |
| 5,491,084 A | 2/1996 | Chalfie et al. | |
| 5,503,974 A | 4/1996 | Gruber et al. | |
| 5,512,421 A | 4/1996 | Burns et al. | |
| 5,591,624 A | 1/1997 | Barber et al. | |
| 5,681,746 A | 10/1997 | Bodner et al. | |
| 5,723,287 A | 3/1998 | Russell et al. | |
| 5,723,333 A | 3/1998 | Levine et al. | |
| 5,739,018 A | 4/1998 | Miyanohara et al. | |
| 5,747,243 A | 5/1998 | Gruber et al. | |
| 5,750,396 A | 5/1998 | Yang et al. | |
| 5,910,434 A | 6/1999 | Rigg et al. | |
| 6,306,434 B1 | 10/2001 | Hong et al. | |
| 7,033,595 B1 | 4/2006 | Sanders et al. | |
| 2005/0112098 A1 | 5/2005 | McCray, Jr. et al. | |

FOREIGN PATENT DOCUMENTS

| | | |
|---|---|---|
| WO | WO 00/08131 A2 | 2/2000 |
| WO | WO 00/08131 A3 | 6/2000 |
| WO | WO 01/83730 A2 | 11/2001 |
| WO | WO 01/83730 A3 | 5/2002 |
| WO | WO 03/014367 A1 | 2/2003 |
| WO | WO 03/035849 A2 | 5/2003 |
| WO | WO 03/035849 A3 | 10/2003 |
| WO | WO 03/102219 A2 | 12/2003 |
| WO | WO 03/102219 A3 | 10/2004 |

OTHER PUBLICATIONS

Kobinger GP et al. "Filovirus-pseudotyped lentiviral vector can efficiently and stably transduce airway epithelia in vivo". Nat Biotechnol. Mar. 2001;19(3):225-30.*
Soneoka Y, et al. "A transient three-plasmid expression system for the production of high titer retroviral vectors." Nucleic Acids Res. Feb. 25, 1995;23(4):628-33.*
Brindley, Ma et al "Ebola Virus Glycoprotein 1: Identification of Residues Important for Binding and Postbinding Events" J. Virol. 2007 81: 7702-7709.*
Yang S, et al. "Generation of retroviral vector for clinical studies using transient transfection." Hum Gene Ther. Jan. 1, 1999;10(1):123-32.*
Abell and Brown, "Sindbis virus membrane fusion is mediated by reduction of glycoprotein disulfide bridges at the cell surface," Sep. 1993 *J. Virol.* 67(9):5496-5501.
Cassell et al., "Effects of lysosomotropic weak bases on infection of BHK-21 cells by Sindbis virus," Dec. 1984 *J. Virol* 52(3):857-864.
Chalfie et al., "Green fluorescent protein as a marker for gene expression," Feb. 11, 1994 *Science* 263(5148):802-805.
Cheng et al., "Nucleocapsid and glycoprotein organization in an enveloped virus," Feb. 24, 1995 *Cell* 80:621-630.
Chepurnov et al., "Suppressive effect of Ebola virus on T cell proliferation in vitro is provided by a 125-kDa GP viral protein," Jun. 1, 1999 *Immunol. Lett.* 68(2-3):257-261.
DeTulleo and Kirchhausen, "The clathrin endocytic pathway in viral infection," 1998*EMBO J.* 17(16):4585-4593.
"The DNA and RNA Reverse Trascribing Viruses," [online]. The International Committee on Taxonomy of Viruses, Apr. 21, 1998 [retrieved Jun. 3, 2003]. Retrieved from the Internet: http://www.ncbi.nlm.nih.gov/ICTV/overview/dnaandrna.html>; 1 pg.
Flynn et al., "A conformational change in Sindbis virus glycoproteins E1 and E2 is detected at the plasma membrane as a consequence of early virus-cell interaction," Aug. 1990*J. Virol.* 64(8):3643-3653.
Fuller, "The T=4 envelope of Sindbis virus is organized by interactions with a complementary T=3 capsid," Mar. 27, 1987 *Cell* 48:923-934.
Gaedigk-Nitschko and Schlesinger, "The sindbis virus 6K protein can be detected in virions and is acylated with fatty acids," Mar. 1990 *Virology* 175(1):274-281.

(Continued)

*Primary Examiner* — Bo Peng
(74) *Attorney, Agent, or Firm* — Mueting Raasch & Gebhardt, P.A.

(57) ABSTRACT

Pseudotyped retroviruses having viral glycoproteins with modified O glycosylation regions are provided. Also provided are methods for making the pseudotyped retroviruses of the present invention and for using the pseudotyped retroviruses for transduction of target cells. Cells for stably producing the pseudotyped retroviruses or the present invention are also provided.

7 Claims, 32 Drawing Sheets

OTHER PUBLICATIONS

Gallardo et al., "Recombinant retroviruses pseudotyped with the vesicular stomatitis virus G glycoportein mediate both stable gene transfer and pseudotransduction in human peripheral blood lymphocytes," Aug. 1, 1997 *Blood* 90(3):952-957.

Glomb-Reinmund and Kielian, "The role of low pH and disulfide shuffling in the entry and fusion of Semliki Forest virus and Sindbis virus," Sep. 1, 1998 *Virology* 248(2):372-381.

Havenga et al., "Development of safe and efficient retroviral vectors for Gaucher disease," Dec. 1997 *Gene Therapy* 4(12):1393-1400.

Liu et al., "Pseudotransduction of hepatocytes by using concentrated pseudotyped vesicular stomatitis virus G glycoprotein (VSV-G)-Moloney murine leukemia virus-derived retrovirus vectors: comparison of VSV-G and amphotropic vectors for hepatic gene transfer," Apr. 1996 *J. Virol.* 70(4):2497-2502.

McCray, Paul "Gene Transfer to Human Airway Epithelia In Vivo," Grant Abstract, Grant No. 2PO1HL051670-06A10005 [online]. National Institutes of Health: National Heart, Lung, and Blood Institute, project datesApr. 1, 1999 to Mar. 31, 2000 [retrieved on Jan. 26, 2005]. Retrieved from the Internet: <http://crisp.cit.nih.gov/crisp/CRISP_LIB.getdoc?textkey=6110285&p_grant_num=2P01HL051670-06A10005&p_query=&ticket=50955150&p_audit_session_d=278722693&p_keywords=>; 2 pgs.

McCray, Paul "Gene Transfer to Human Airway Epithelia In Vivo," Grant Abstract, Grant No. 5PO1HL051670-070005 [online]. National Institutes of Health: National Heart, Lung, and Blood Institute, project dates Jul. 1, 2000 to Mar. 31, 2001 [retrieved on Jan. 26, 2005]. Retrieved from the Internet: <http://crisp.cit.nih.gov/crisp/CRISP_LIB.getdoc?textkey=6325956&p_grant_num=5P01HL051670-070005&p_query=&ticket=50955150&p_audit_session_id=278722693&p_keywords=>; 2 pgs.

McCray, Paul "Gene Transfer to Human Airway Epithelia In Vivo," Grant Abstract, Grant No. 5PO1HL051670-080005 [online]. National Institutes of Health: National Heart, Lung, and Blood Institute, project dates Aug. 1, 2001 to Mar. 31, 2002 [retrieved on Jan. 26, 2005]. Retrieved from the Internet: <http://crisp.cit.nih.gov/crisp/CRISP_LIB.getdoc?textkey=6485289&p_grant_num=5P01HL051670-080005&p_query=&ticket=50955150&p_audit_session_id=278722693&p_keywords=>; 2 pgs.

McCray, Paul "Gene Transfer to Human Airway Epithelia In Vivo," Grant Abstract, Grant No. 5PO1HL051670-090005 [online]. National Institutes of Health: National Heart, Lung, and Blood Institute, project dates Apr. 1, 2002 to Mar. 31, 2003 [retrieved on Jan. 26, 2005]. Retrieved from the Internet: <http://crisp.cit.nih.gov/crisp/CRISP_LIB.getdoc?textkey=6581185&p_grant_num=5P01HL051670-090005&p_query=&ticket=50955150&p_audit_session_id=278722693&p_keywords=>; 2 pgs.

McCray, Paul "Gene Transfer to Human Ainvay Epithelia In Vivo," Grant Abstract, Grant No. 5PO1HL051670-100005 [online]. National Institutes of Health: National Heart, Lung, and Blood Institute, project dates unlisted [retrieved on Jan. 26, 2005]. Retrieved from the Internet: <http://crisp.cit.nih.gov/crisp/CRISP_LIB.getdoc?textkey=6729317&p_grant_num=5P01HL051670-100005&p_query=&ticket=50955150&p_audit_session_id=278722693&p_keywords=>; 2 pgs.

McCray, Paul "Targeting Entry in Epithelia with ICMV-FIV," Grant Abstract, Grant No. 2PO1HL051670-110005 [online]. National Institutes of Health: National Heart, Lung, and Blood Institute, project dates Apr. 1, 2004 to Mar. 31, 2009 [retrieved on Jan. 26, 2005]. Retrieved from the Internet: <http://crisp.cit.nih.gov/crisp/CRISP_LIB.getdoc?textkey=6853152&p_grant_num=2PO1HL051670-110005&p_query=&ticket=50955150&p_audit_session_id=278722693&p_keywords=>; 2 pgs.

McCray, Paul "Innate Immune Properties of Airway Epithelium," Grant Abstract, Grant No. 2P50HL061234-060002 [online]. National Institutes of Health: National Heart, Lung, and Blood Institute, project dates Sep. 1, 2003 to Aug. 31, 2008 [retrieved on Jan. 26, 2005]. Retrieved from the Internet: <http://crisp.cit.nih.gov/crisp/CRISP_LIB.getdoc?textkey=6716915&p_grant_num=2P50HL061234-060002&p_query=&ticket=58832430&p_audit_session_id=296592937&p_keywords=; 2 pgs.

McCray, Paul "Innate Immune Properties of Airway Epithelium," Grant Abstract, Grant No. 5P50HL061234-070002 [online]. National Institutes of Health: National Heart, Lung, and Blood Institute, Fiscal Year 2004, [retrieved on Jan. 26, 2005]. Retrieved from the Internet: <http://crisp.cit.nih.gov/crisp/CRISP_LIB.getdoc?textkey=6948852&p_grant_num=5P50HL061234-070002&p_query=&ticket=58832430&p_audit_session_d=296592937&p_keywords=>; 2 pgs.

McCray, Paul "Retrovirus Mediated Gene Transfer to Airway Epithelia," Grant Abstract, Grant No. 1RO1HL061460-01 [online]. National Institutes of Health: National Heart, Lung, and Blood Institute, project dates Dec. 16, 1998 to Nov. 30, 2002 [retrieved on Jan. 26, 2005]. Retrieved from the Internet: <http://crisp.cit.nih.gov/crisp/CRISP_LIB.getdoc?textkey=2732174&p_grant_num=1R01HL061460-01&p_query=&ticket=50955150&p_audit_session_id=278722693&p_keywords=>; 2 pgs.

McCray, Paul "Retrovirus Mediated Gene Transfer to Airway Epithelia," Grant Abstract, Grant No. 5RO1HL061460-02 [online]. National Institutes of Health: National Heart, Lung, and Blood Institute, project dates Dec. 16, 1998 to Nov. 30, 2002 [retrieved on Jan. 26, 2005]. Retrieved from the Internet: <http://crisp.cit.nih.gov/crisp/CRISP_LIB.getdoc?textkey=6125979&p_grant_num=5R01HL061460-02&p_query=&ticket=50955150&p_audit_session_id=278722693&p_keywords=>; 2 pgs.

McCray, Paul "Retrovirus Mediated Gene Transfer to Ainvay Epithelia," Grant Abstract, Grant No. 5RO1HL061460-03 [online]. National Institutes of Health: National Heart, Lung, and Blood Institute, project dates Dec. 16, 1998 to Nov. 30, 2002 [retrieved on Jan. 26, 2005]. Retrieved from the Internet: <http://crisp.cit.nih.gov/crisp/CRISP_LIB.getdoc?textkey=6330181&p_grant_num=5R01HL061460-03&p_query=&ticket=50955150&p_audit_session_id=278722693&p_keywords=>; 2 pgs.

McCray, Paul "Retrovirus Mediated Gene Transfer to Airway Epithelia," Grant Abstract, Grant No. 5RO1HL061460-04 [online]. National Institutes of Health: National Heart, Lung, and Blood Institute, project dates Dec. 16, 1998 to Nov. 30, 2003 [retrieved on Jan. 26, 2005]. Retrieved from the Internet: <http://crisp.cit.nil.gov/crisp/CRISP_LIB.getdoc?textkey=6476880&p_grant_num=5R01HL061460-04&p_query=&ticket=50955150&p_audit_session_id=278722693&p_keywords=>; 2 pgs.

McCray, Paul "Filovirus Enveloped FIV: Virus-epithelia Interactions-CF," Grant Abstract, Grant No. 1RO1HL075363-01 [online]. National Institutes of Health: National Heart, Lung, and Blood Institute, project dates Apr. 1, 2004 to Mar. 31, 2008 [retrieved on Jan. 26, 2005]. Retrieved from the Internet: <http://crisp.cit.nih.gov/crisp/CRISP_LIB.getdoc?textkey=6709619&p_grant_num=1R01HL075363-01&p_query=&ticket=50955150&p_audit_session_id=278722693&p_keywords=>; 2 pgs.

"NetOGlyc 2.0 Server" [online]. Center for Biological Sequence Analysis, Feb. 24, 2003 [retrieved Jun. 3, 2003]. Retrieved from the Internet: <http://www.cbs.dtu.dk/services/NetOGlyc/>; 2 pgs.

Rolls et al., "Novel infectious particles generated by expression of the vesicular stomatitis virus glycoprotein from a self-replicating RNA," Nov. 4, 1994 *Cell* 79:497-506.

Schnierle et al., "Pseudotyping of murine leukemia virus with the envelope glycoproteins for HIV generates a retroviral vector with specificity of infection for CD4-expressing cells," Aug. 5, 1997 *PNAS* 94(16):8640-8645.

Simmons et al., "Ebola virus glycoproteins induce global surface protein down-modulation and loss of cell adherence," Mar. 2002 *J. Virol.* 76(5):2518-2528.

Sinn, Patrick "Pseudotyping FIV to Target Human Airway Epithelia," Grant Abstract, Grant No. 1F32HL067623-01 [online]. National Institutes of Health; National Heart, Lung, and Blood Institute, project start date Sep. 12, 2001 [retrieved on Jan. 26, 2005]. Retrieved from the Internet: <http://crisp.cit.nih.gov/crisp/CRISP_LIB.getdoc?textkey=6340380&p_grant_num=1F32HL067623-01&p_query=&ticket=50955893&p_audit_session_id=278722693&p_keywords=>; 2 pgs.

Sinn, Patrick "Pseudotyping FIV to Target Human Airway Epithelia," Grant Abstract, Grant No. 5F32HL067623-02 [online]. National Institutes of Health; National Heart, Lung, and Blood Institute, project start date Sep. 12, 2002 [retrieved on Jan. 26, 2005]. Retrieved from the Internet: <http://crisp.cit.nih.gov/crisp/CRISP_LIB.getdoc?textkey=6555856&p_grant_num=5F32HL067623-02&p_query=&ticket=50955893&p_audit_session_id=278722693&p_keyvvords—>; 2 pgs.
Wahlberg et al., "Membrane fusion of Semliki Forest virus involves homotrimers of the fusion protein," Dec. 1992 *J. Virol.* 66(12):7309-7318.
Wahlberg and Garoff, "Membrane fusion process of Semliki Forest virus. I: Low pH-induced rearrangement in spike protein quaternary structure precedes virus penetration into cells," Jan. 1992 *J. Cell. Biol.* 116(2):339-348.
American Type Culture Collection, "ATTC No. CRL-1573," organism: *Homo sapiens* (human); designation: 293 [HEK-293] [online]; Manassas, VA [retrieved on Nov. 13, 2007] from the Internet. Retrieved from the Internet: <http://www.atcc.org/common/catalog/numSearch/numResults.cfm>; 4 pgs.
American Type Culture Collection, "ATTC No. CRL-1658," organism: *Mus musculus* (mouse); designation: NIH/3T3 [online]; Manassas, VA [retrieved on Nov. 13, 2007] from the Internet. Retrieved from the Internet: <http://www.atcc.org/common/catalog/numSearch/numResults.cfm>; 3 pgs.
Ausubel et al., eds., *Current Protocols in Molecular Biology*, John Wiley & Sons, Inc., New York, NY, 1988; title page, publisher's page and table of contents (14 pages).
Blanton et al., "Plasmid transfection and retroviral transduction of porcine muscle cells for cell-mediated gene transfer," 2000 *J. Anim. Sci.* 78(4):909-918.
Boucher, "Status of gene therapy for cystic fibrosis lung disease" *J. Clin. Invest.* 1999;103:441-445.
Chan et al. "Distinct mechanisms of entry by envelope glycoproteins of Marburg and Ebola (Zaire) viruses", *J. Virol* 2000; 74(10):4933-4937.
Chan et al. "Folate receptor-alpha is a cofactor for cellular entry by Marburg and Ebola viruses" *Cell* 2001;106:117-26.
Coffin et al., *Retroviruses*. Cold Spring Harbor Laboratory Press: Plainview, NY; 2000. Online book [retrieved Nov. 15, 2007]. Retrieved from the Internet: <http://www.ncbi.nlm.nih.gov/books/bv.fcgi?call=bv.View..ShowTOC&rid=rv.TOC&depth=10>; Title and table of contents (5 pgs.).
Crystal, "Transfer of genes to humans: early lessons and obstacles to success," 1995 *Science* 270:404-410.
Delos et al. "Critical role for the cysteines flanking the internal fusion peptide of avian sarcoma/leukosis virus envelope glycoprotein" *J. Virol.* 2000;74:9738-9741.
Deonarain "Ligand-targeted receptor-mediated vectors for gene delivery," 1998 *Exp. Opin. Ther. Patents* 8(1):53-69.
Dobson, "Gene therapy progress and prospects: magnetic nanoparticle-based delivery," 2006 *Gene Ther.* 13(4):283-287.
Dong et al., "A chimeric avian retrovirus containing the influenza virus hemagglutinin gene has an expanded host range," 1992 *J. Virol.* 66:7374-7382.
"Ebola virus used in study: UI research may aid cystic fibrosis therapy" *Iowa City Press-Citizen* Apr. 30, 2003; Retrieved from: http://www.press-citizen.com/news/043003ebola.htm. On May 2, 2003.

Ellgaard et al., "Setting the standard: quality control in the secretory pathway," 1999 *Science* 286:1882-1888.

Elroy-Stein et al. "Cap-independent translation of mRNA conferred by encephalomyocarditis virus 5' sequence improves the performance of the vaccinia virus/bacteriophage T7 hybrid expression system" *Proc Natl Acad Sci USA* 1989;86:6126-6130.

Faragher et al. "Genome Sequences of a Mouse-Avirulent and a Mouse-Virulent Strain of Ross River Virus" *Virology* 1988;163(2):509-526.

Fass et al., "Retrovirus envelope domain at 1.7 Angstrom resolution," 1996 *Nat. Struct. Bio*. 3:465-469.

Feldmann et al., "Characterization of filoviruses based on differences in structure and antigenicity of the virion glycoprotein," 1994 *Virology* 199:469-473.

Feldmann et al., "The glycoproteins of Marburg and Ebola virus and their potential roles in pathogenesis," 1999 *Arch. Virol. Supp*.15:159-169.

Felkner et al. "Mutational analysis of the N-linked glycosylation sites of the SU envelope protein of Moloney murine leukemia virus" *J. Virol*. 1992;66:4258-4264.

Ferry et al., "Liver-directed gene transfer vectors," 1998 *Hum. Gene Ther*. 9:1975-1981.

Gallaher "Similar structural models of the transmembrane proteins of Ebola and avian sarcoma viruses," 1996 *Cell* 85:477-478.

Grignani et al. "High-Efficiency Gene Transfer and Selection of Human Hematopoietic Progenitor Cells with a Hybrid EBV/Retroviral Vector Expressing the Green Fluorescence Protein", *Cancer Research* 1998;58:14-19.

Hansen et al., "Prediction of O-glycosylation of mammalian proteins: specificity patterns of UDP-GalNAc:polypeptide N-acetylgalactosaminyltransferase," 1995 *Bioc. J*. 308:801-813.

Hansen et al. "O-glycbase version 2.0—A revised database of O-glycosylated proteins" *Nucleic Acids Research* 1997;25:278-282.

Hansen et al."NetOglyc: Prediction of mucin type O-glycosylation sites based on sequence context and surface accessibility" *Glycoconjugate Journal* 1998;15:115-130.

Hatziioannou et al. "Incorporation of Fowl Plague Virus Hemagglutinin into Murine Leukemia Virus Particles of Analysis of the Infectivity of the Pseudotyped Retroviruses" *J. of Virology* 1998; 72:5313-5317.

Ito et al., "Mutational analysis of the putative fusion domain of Ebola virus glycoprotein," 1999 *J. Virol* 73:8907-8912.

Ito et al., "Ebola virus glycoprotein: proteolytic processing, acylation, cell tropism, and detection of neutralizing antibodies," 2001 *J. Virol* 75:1576-1580.

Jeffers et al. "Covalent modifications of the ebola virus glycoprotein." *J. Virol*. 2002; 76(24):12463-72.

Johnson et al. "Pseudotyped human lentiviral vector-mediated gene transfer to airway epithelia in vivo" *Gene Therapy* 2000;7:568-574.

Johnston et al. "Minimum Requirements for Efficient Transduction of Dividing and Nondividing Cells by Feline Immunodeficiency Virus Vector" *J. Virol*. 1999; 73(6):4991-5000.

Kang et al. "In vivo gene transfer using a nonprimate lentiviral vector pseudotyped with Ross River Virus glycoproteins." *J Virol*. 2002; 76(18):9378-88.

Kayman et al. "Mutational analysis of N-linked glycosylation sites of Friend murine leukemia virus envelop protein" *J. Virol*. 1991;65:5323-5332.

Kobinger et al. "Filovirus-pseuodtyped lentiviral vector can efficiently and stably transduce airway epithelia in vivo" *Nat. Biotechnol*. 2001;19(3):225-30.

Kuhn et al. "Infectious RNA Transcripts from Ross River Virus cDNA Clones and the Construction and Characterization of Defined Chimeras with Sindbis Virus" *Virology* 1991; 182:430-441.

Kuhn et al. "Chimeric Sindbis-Ross River Viruses to Study Interactions Between Alphavirus Nonstructural and Structural Regions" *J. of Virology* 1996; 70(11):7900-7909.

Li et al. "The critical N-linked glycan of murine leukemia virus envelope protein promotes both folding of the C-terminal domains of the precursor polyprotein and stability of the postcleavage envelope complex" *J. Virol*. 1997; 71:7012-7019.

Lodge et al. "Two distinct oncornaviruses harbor an intracytoplasmic tyrosine-based basolateral targeting signal in their viral envelope glycoprotein." *J Virol*. 1997; 71(7):5696-702.

Lopez et al. "Nucleocapsid-Glycoprotein Interactions Required for Assembly of Alphaviruses" *J. of Virology* 1994 68:1316-1323.

Malashkevich et al., "Core structure of the envelope glycoprotein GP2 from Ebola virus at 1.9 A resolution," 1999 *PNAS* 96:2662-2667.

Markowitz et al. "A safe packaging line for gene transfer: separating viral genes on two different plasmids." *J Virol*. 1988;62(4):1120-4.

Marsh et al. "Virus entry into animal cells." in *Adv Virus Res* vol. 36. Maramorosch et al. (Eds.). Academic Press: San Diego, CA. 1989. Title page, publishers page, and pp. 107-151.

McCray, Jr. "Difficulties of gene therapy" 2001 *The Lancet Supplement* 358-Cystic Fibrosis:S19.

McCray, Jr. et al., "Development of Pseudotyped FIV-based Lentiviral Vectors for Efficient Gene Transfer to Airway Epithelia," $2^{nd}$ Annual Gene Therapy Symposium for Heart, Lung, and Blood Diseases, National Heart, Lung, and Blood Institute, Sonoma, California, Nov. 20 and 21, 2003; 2 pgs.

Medina et al. "Lentiviral Vectors Pseudotyped with Minimal Filovirus Envelopes Increased Gene Transfer in Murine Lung" *Molecular Therapy* 2003;8(5):777-789.

Miller and Vile "Targeted vectors for gene therapy," 1995 *FASEB J.* 9(2):190-199.
Morgenstern et al. "A series of mammalian expression vectors and characterisation of their expression of a reporter gene in stably and transiently transfected cells." *Nucleic Acids Res*. 1990;18(4):1068.
Mosbys 2004 Drug Guide Mosbys, Inc: St. Louis, MO; 2004. Title page, publisher's page, and table of contents.
National Center for Biotechnology Information, National Library of Medicine, National Institutes of Health. GenBank Locus NC_001608, Accession No. NC_001608, "Lake Victoria marburgvirus—Musoke, complete genome," Bethesda, MD. Available online [retrieved Nov. 13, 2007]. Retrieved from the Internet: <http://www.ncbi.nlm.nih.gov/entrez/viewer.fcgi?db=nuccore&id=158539108>; 10 pgs.
National Center for Biotechnology Information, National Library of Medicine, National Institutes of Health. GenBank Locus NC_002549, Accession No. NC_002549, "Zaire ebolavirus, complete genome," Bethesda, MD. Available online [retrieved Nov. 13, 2007]. Retrieved from the Internet: <http://www.ncbi.nlm.nih.gov/entrez/viewer.fcgi?db=nuccore&id=10313991>; 13 pgs.
National Center for Biotechnology Information, National Library of Medicine, National Institutes of Health. GenBank Locus EVU23069, Accession No. U23069, "Sudan Ebola virus Maleo strain glycoprotein (GP) gene, complete cds," Bethesda, MD. Available online [retrieved Nov. 13, 2007]. Retrieved from the Internet: <http://www.ncbi.nlm.nih.gov/entrez/viewer.fcgi?db=nuccore&id=1041198>; 3 pgs.
National Center for Biotechnology Information, National Library of Medicine, National Institutes of Health. GenBank Locus EVU23152, Accession No. U23152, "Reston Ebola virus glycoprotein (GP) gene, complete cds," Bethesda, MD. Available online [retrieved Nov. 13, 2007]. Retrieved from the Internet: <http://www.ncbi.nlm.nih.gov/entrez/viewer.fcgi?db=nuccore&id=1041201>; 3 pgs.
National Center for Biotechnology Information, National Library of Medicine, National Institutes of Health, GenBank Locus EVU23187, Accession No. U23187, "Zaire Ebola virus Mayinga strain glycorotein (GP) gene, compete cds." Bethesda, MD. Available online [retrieved Feb. 8, 2003]. Retrieved from the Internet: <http://www.ncbi.nlm.nih.gov/entrez/query.fcgi?cmd=Retrieve&db=nucleotide&list_uids=10>; 3 pgs.
National Center for Biotechnology Information, National Library of Medicine, National Institutes of Health, GenBank Locus MVREPCYC, Accession No. Z12132 S55429, "*Marburg virus genes fro vp35,vp40, vp30, vp24, glycoprotein, nucleoprotein, polymerase*," Bethesda, MD. Available online [retrieved Aug. 26, 2002]. Retrieved from the Internet: <http://www.ncbi.nlm.nih.gov/entrez/query.fcgi?cmd—Retrieve&db=Nucleotide&list_uids=5>; 11 pgs.
National Center for Biotechnology Information, National Library of Medicine, National Institutes of Health, GenBank Locus MVREPCYC, Accession No. Z12132 GI: 541780, "*Marburg virus genes for vp35, vp40, vp30 vp24, glycoprotein, nucleoprotein, polymerase*," Bethesda, MD. Available online [retrieved Feb. 8, 2003]. Retrieved from the Internet: <http://www.ncbi.nlm.nih.gov/entrez/viewer.fcgi?cmd=&txt=&save=&cfm=&query_key=2&db=nucleotide&Extrafeat=-1&view+def&dispmax=20&SendTo=on&from=5822&_to8666&_Strand=,>; 3 pgs.
Oliver et al. "ERp57 functions as a submit of specific complexes formed with the ER lectins calreticulin and calnexin" *Mol. Biol. Cell* 1999;10:2573-2582.
Ory et al. "A Stable Human-Derived Packaging Cell Line for Production of High Titer Retrovirus/Vesicular Stomatitis Virus G Pseudotypes" *Proc. Nat'l. Acad. Sci USA* 1996;93:11400-11406.
Pear et al. "Production of high-titer helper-free retroviruses by transient transfection" *Proc Natl Acad Sci USA*. 1993;90(18):8392-6.
Pinter et al., "Localization of the labile disulfide bond between SU and TM of the murine leukemia virus envelope protein complex wtoa highly conserved CWLC motif in SU that resembles the active site sequence of thiol-disulfide exchange enzymes," 1997 *J. Virol.* 71:8073-8077.
Pouton and Seymour, "Key issues in non-viral gene delivery," 2001 *Adv. Drug Deliv. Rev.* 46(1-3):187-203.
Prasher et al. "Primary structure of the Aequorea victoria green-fluorescent protein." *Gene*. 1992;111(2):229-33.
Read et al., "Barriers to gene delivery using synthetic vectors," 2005 *Adv. Genet.* 53PA:19-46.
Riviere et al. "Effects of Retroviral Vector Design on Expression of Human Adenosine Deaminase in Murine Bone Marrow Transplant Recipients Engrafted with Genetically Modified Cells" *Proc. Nat'll Acade Sci. USA* 1995;92:6733-6737.
Ruiz-Arguello et al., "Phosphatidyulinositol-dependent membrane fusion induced by a putative fusogenic sequence of Ebola virus," 1998 *J. Virol*. 72:1775-1781.
Sambrook et al. (Eds.) *Molecular Cloning, A Laboratory Manual*, Cold Spring Harbor Laboratory Press, Cold Spring Harbor, NY, 2000. Title page, publisher's page, and table of contents only; 18 pgs.
Sanchez et al. "Sequence Analysis of the Ebola Virus Genome: Organization, Genetic Elements, and Comparison with the Genome of Marburg Virus" *Virus Research* 1993;29(3):215-240.
Sanchez et al. "The virion glycoproteins of Ebola viruses are encoded in two reading frames and are expressed through transcriptional editing" *Proc Natl. Acad. Sci USA* 1996;93:3602-3607.
Sanchez et al. "Biochemical analysis of the secreted and virion glycoproteins of Ebola virus" *J. Virol*. 1998;72:6442-6447.
Sanders, David. 5$^{th}$ Annual American Society of Gene Therapy Meeting. Jun. 5-9, 2002 in Boston, Massachusetts. Oral Presentation. Jun. 6, 2002.
Sanders, "No false start for novel pseudotyped vectors."*Curr Opin Biotechnol*. 2002; 13(5):437-42.
Sanders. "Sulfhydrol involvement in fusion mechanisms" in H. Hilderson and S. Fuller (ed.), *Fusion of biological membranes and related problems*. Kluwer Academic/Plenum Publishers, New York.. 2000. Title page, table of contents, and pp. 483-514.
Sanders et al., "Ebola virus glycoproteins: guidance devices for targeting gene therapy cevtors," 2004 *Expert Opin Biol. Ther*. 4(3):329-336.
Sanes et al. "Use of a recombinant retrovirus to study post-implantation cell lineage in mouse embryos." *EMBO J.* 1986;5(12):3133-42.
Scheetz et al. "Genomics based approaches to gene discovery in innate immunity." *Immunol Rev.* 2002; 190:137-45.
Sharkey et al."Ross River Virus Glycoprotein-Pseudotyped Retroviruses and Stable Cell Lines for Their Production" 2001 *J. Virol*. 75(6):2653-2659.
Sharma et al. "Efficient Infection of a Human T-Cell Line and of Human Primary Peripheral Blood Leukocytes with a Pseudotyped Retrovirus Vector" *Proc. Nat'l Acad. Sci. USA* 1996 ;93(21):11842-11847.
Shinnick et al."Nucleotide sequence of Moloney murine leukaemia virus." 1981 *Nature* 293(5833):543-548.
Sinn et al., "Folate Receptor Alpha-Dependent and Independent Pathways for Entry of Filovirus Glycoprotein Pseudotyped Feline Immunodeficiency Virus (FIV)-Based Vectors Into Human Airway Epithelia", Abstract No. 208. The Sixteenth Annual North American Cystic Fibrosis Conference, The Cystic Fibrosis Foundation, New Orleans, Louisiana, Oct. 3-6, 2002; 2 pgs.
Sinn et al. "Lentivirus Vectors Pseudotyped with Filoviral Envelope Glycoproteins Transduce Airway Epithelia from the Apical Surface Independently of Folate Receptor Alpha" *J. of Virology* 2003;77(10):5902-5910.
Sinn et al., "Pseudotyping FIV-based lentiviral vectors: Three glycoproteins that confer apical entry to airway epithelia," 2$^{nd}$ Annual Gene Therapy Symposium for Heart, Lung, and Blood Diseases, National Heart, Lung, and Blood Institute, Sonoma, California, Nov. 20 and 21, 2003; 2 pgs.
Sinn et al., "Targeting Apical Entry in Airway Epithelia Using Pseudotyped FIV-Based Lentiviral Vectors," The Seventeenth Annual North American Cystic Fibrosis Conference. Abstract No. 212, The Cystic Fibrosis Foundation, Anaheim, California, Oct. 16-19, 2003; 2 pgs.

Smith et al. "Putative receptor binding sites on alphaviruses as visualized by cryoelectron microscopy." *Proc Natl Acad Sci USA.* 1995;92(23):10648-52.

Strauss et al. "The alphaviruses: gene expression, replication, and evolution." *Microbiol Rev.* 1994;58(3):491-562.

Swift et al. "Rapid production of retroviruses for efficient gene delivery to mammalian cells using 293T Cell-Based systems," in R. Cico (ed.), *Current Protocols in Immunology* suppl. 31. J. Wiley & Sons: Hoboken, NJ; 1999. Title page, publishers page and pp. 10.17.14-10.17.29.

Taggart et al. A Putative Role of Elastolytic Cathepsins in the Diminution of the Antimicrobial Defenses in Cystic Fibrosis Abstract No. 287.The Seventeenth Annual North American Cystic Fibrosis Conference. The Cystic Fibrosis Foundation, Anaheim, California, Oct. 16-19, 2003; 2 pgs.

Takada et al. "A System for Functional Analysis of Ebola Virus Glycoprotein" *Proc. Nat'l Acad. Sci. USA* 1997; 94:14764-14769.

Taylor and Sanders, "The role of the membrane-spanning-domain sequence in glycoprotein-mediated membrane fusion," 1999 *Mol. Biol. Cell* 10:2803-2815.

Taylor et al. "Fv-4: identification of the defect in Env and the mechanism of resistance to ecotropic murine leukemia virus." *J Virol.* 2001;75(22):11244-8.

Thomas et al. "Analysis of cysteine mutations on the transmembrane protein of Moloney murine leukemia virus" *Virology* 1995;211:285-289.

Van Beveren et al. "Nucleotide sequence of the genome of a murine sarcoma virus." *Cell* 1981;27(1 Pt 2):97-108.

Verhoeyen et al., "Surface-engineering of lentiviral vectors," 2004 *J. Gene Med.* 6 Supp 1:S83-94.

Verma and Somia, "Gene therapy—promises, problems, and prospects," 1997 *Nature* 389:239-242.

Volchkov et al. "The envelope glycoprotein of Ebola virus contains an immunosuppressive-like domain similar to oncogenic retroviruses" *FEBS Lett* 1992; 305:181-184.

Volchkov et al., "GP mRNA of Ebola virus is edited by the Ebola virus polymerase and by T7 and vaccinia virus polymerases," 1995 *Virology* 214:421-430.

Volchkov et al., "Processing of the Ebola virus glycoprotein by the proprotein convertase furin," 1998 *PNAS* 95:5762-5767.

Volchkov et al. "Release of viral glycoproteins during Ebola virus infection" *Virology* 1998;245:110-119.

Volchkov et al. "Recovery of infectious Ebola virus from complementary DNA: RNA editing of the GP gene and viral cytotoxicity" *Science* 2001;291:1965-9.
Vochkova et al., "The nonstructural small glycoprotein sGP of Ebola virus is secreted as an antiparallel-oriented homodimer," 1998 *Virology* 250:408-414.
Volchkova et al., "Delta-peptide is the carboxy-terminal cleavage fragment of the nonstructural small glycoprotein sGP of Ebola virus," 1999 *Virology* 265:164-171.
Wang et al. "Feline immunodeficiency virus vectors persistently transduce nondividing airway epithelia and correct the cystic fibrosis defect" 1999 *J. Clin. Invest*. 104;R55-62.
Wang et al., "Development of retroviral vectors for gene transfer to airway epithelia," 2000 *Curr. Opin. Mol. Ther.* 2(5):497-506.
Wang et al., "Apical barriers to airway epithelial cell gene transfer with amphotropic retroviral vectors," 2002 *Gene Therapy* 9(14):922-931.
Wang et al., "Gene transfer to airway epithelia using feline immunodeficiency virus-based lentivirus vectors," 2002 *Methods Enzymology* 346:500-514.
Watson et al. "Targeted Transduction Patterns in the Mouse Brain by Lentivirus Vector Pseudotyped with VSV, Ebola, Mokola, LCMV, or MuLV Envelope Proteins" *Molecular Therapy* 2002; 5(5):Part 1 of 2, 528-537.
Weissenhorn et al., "Crystal structure of the Ebola virus membrane fusion subunit GP2, from the envelope glycoprotein ectodomain," 1998 *Mol. Cell* 2:605-616.
Will et al. "Marburg Virus Gene 4 Encodes the Virion Membrane Protein, a Type I Transmembrane Glycoprotein", *J. of Virology* 1993;67(3):1203-1210.
Wilson et al. "Epitope involved in antibody-mediated protection from ebola virus" 2000 *Science* 287:1664-6.
Wool-Lewis and Bates, "Characterization of Ebola virus entry to using pseudotyped viruses: identification of receptor-deficient cell lines," 1998 *J. Virol* 72:3155-3160.
Wool-Lewis and Bates, "Endoproteolytic processing of the Ebola virus envelope glycoprotein: cleavage is not required for function," 1999 J. Virol 73:1419-1426.
Yang et al. "Distinct Cellular Interactions of Secreted and Transmembrane Ebola Virus Glycoproteins" *Science* 1998;279:1034-1037.
Yang et al. "Identification of the Ebola virus glycoprotein as the main viral determinant of vascular cell cytotoxicity and injury" *Nat. Med*. 2000;6:886-9.
Yee et al., "A general method for the generation of high-titer, pantropic retroviral vectors: highly efficient infection of hepatocytes," 1994 *PNAS* 91:9564-9568.
Chandran et al., "Endosomal proteolysis of the Ebola virus glycoprotein is necessary for infection," Jun. 10, 2005 *Science* 308:1643-1645. Available online on Apr. 14, 2005.
Kuhn et al., "Conserved receptor-binding domains of Lake Victoria Marburg virus and Zaire Ebolavirus bind a common receptor," Jun. 9, 2006 *J. Biol. Chem.* 281(23):15951-15958. Available online on Apr. 4, 2006.
Manicassamy et al., "Comprehensive analysis of Ebola virus GP1 in viral entry," Apr. 2005 *J. Virology* 79(8):4793-4805.
Manicassamy et al., "Characterization of Marburg virus glycoprotein in viral entry," Feb. 5, 2007 *Virology* 358(1):79-88. Available online on Sep. 20, 2006.
Marzi et al., "The signal peptide of the Ebolavirus glycoprotein influences interaction with the cellular lectins DC-SIGN and DC-SIGNR," Jul. 2006 *J. Virology* 80(13):6305-6317.
Sinn et al., "Persistent gene expression in mouse nasal epithelia following Feline Immunodeficiency Virus-based vector gene transfer," Oct. 2005 *J. Virology* 79(20):12818-12827.

* cited by examiner

*Fig. 1B* pEboGPΔ309-489
6708 base pairs
Unique Sites

- 12 Bgl II
- 206 Nru I
- 228 Mlu I
- 483 Nde I
- 588 SnaB I
- 895 Nhe I
- 908 Afl II
- 911 Hin D III
- 922 Sbf I
- 941 BamH I
- 945 Xcm I
- 990 BspD I
- 990 Cla I
- 1575 Ppu M I
- 1622 Age I
- 2221 Pfl M I
- 2323 BspE I
- 2477 Bpu1102 I
- 2477 Esp I
- 2633 Acc 65 I
- 2633 Asp 718
- 2633 Kpn I
- 2645 EcoR I
- 2671 Not I
- 2678 PaeR7 I
- 2678 Xho I
- 2690 Apa I
- 2903 Bbs I
- 2903 Bbs I
- 2903 Bbv II
- 2903 BpuA I
- 2983 BciV I
- Stu I 3745
- Avr II 3748
- Bss H II 3913
- SgrA I 3990
- Bsm I 4461
- BstZ17 I 4511
- Bst1107 I 4511
- Xca I 4511
- Fsp I 6005
- Pvu I 6152

```
                                    Tfi I
                                    Taq I
                                    Cla I
                                    Sau3A I
                                    Mbo I
                                    Dpn II
                             BssS I     Hinf I
                             Mnl I  BspD I
         Ssp I               Mae III  Dpn I           Mnl I
         Mae III             |  ||   |||  |           |
         |    |              |  ||   |||  |           |
    CGTTACAGGAATATTGCAGTTACCTCGTGATCGATTCAAGAGGACATCATTCTTTCTTTGGGTAATTATCCTTTTCCAAA  1040
    GCAATGTCCTTATAACGTCAATGGAGCACTAGCTAAGTTCTCCTGTAGTAAGAAAGAAACCCATTAATAGGAAAAGGTTT
    |        |          |   |  ||    |||  |            |        .        .         .
    962      970        979  983 989      1000
                            984  990
                                 989
                                 989
                                 989
                                 990
                                  991
                                    993
```

```
                                                       Taq I    Rsa I
                                                       Sal I    Mae I
                                     Fok I             HinC II  Bfa I           Earn1105 I
                                     Ple I             Acc I    Spe I           Mae III
    Rmn I    Fok I    Hinf I                           |   |    |               |  |
    |        |        |                                ||       ||              |  |
    GAACATTTTCCATCCCACTTGGAGTCATCCACAATAGCACATTACAGGTTAGTGATGTCGACAAACTAGTTTGTCGTGAC  1120
    CTTGTAAAAGGTAGGGTGAACCTCAGTAGGTGTTATCGTGTAATGTCCAATCACTACAGCTGTTTGATCAAACAGCACTG
    |        .|       .|        .                      ||  .    ||  .           ||  .
    1041     1051     1062                              1097    1105            1116
                      1062                              1097    1106            1118
                            1066                        1097    1106
                                                        1098    1106
```

```
                                  Mme I
                                  Sau3A I
                                  Mbo I
                                  Dpn II        Taq I
                                  Dpn I         Tfi I
         Fok I    Mun I    Dpn I         Hinf I                             Mae II
         |        |        |             |                                  |
    AAACTGTCATCCACAAATCAATTGAGATCAGTTGGACTGAATCTCGAAGGGAATGGAGTGGCAACTGACGTGCCATCTGC  1200
    TTTGACAGTAGGTGTTTAGTTAACTCTAGTCAACCTGACTTAGAGCTTCCCTTACCTCACCGTTGACTGCACGGTAGACG
    |    .   |        .|   |     .|        |    .             .             |
    1128     1139     1146       1159                                        1188
                      1146       1159
                      1146              1164
                            1151
```

```
              Msp I
              Hpa II
              BsaW I
              Sau96 I
              Ava II      HgiE II          Hph I
         Eco57 I     Bsl I                 Alu I
         |    |  |||      |   |            |   |
    AACTAAAAGATGGGGCTTCAGGTCCGGTGTCCCACCAAAGGTGGTCAATTATGAAGCTGGTGAATGGGCTGAAAACTGCT  1280
    TTGATTTTCTACCCCGAAGTCCAGGCCACAGGGTGGTTTCCACCAGTTAATACTTCGACCACTTACCCGACTTTTGACGA
    |        .    .|  |||     .| |          .             |    |.    .             .
             1216          1231                     1255
             1221     1234                          1259
             1221
                1223
                1224
                1224
```

```
                                                                    Cfr10 I
                                                                    Nla IV
                                                                    Ban I
                                                                    Msp I
                                                                    Hpa II
                                                                    ScrF I
                                    HinP I                          Nci I
                                    Hha I                           Bsl I
                                    Hae II              Tfi I       Bcn I    Msp I
                                    Fnu4H I             Hinf I      Sec I    BsrF I
                    Acc I   Bbv I                                   BsaJ I   Hpa II
                      |       | ||                        |          ||| |   ||
ACAATCTTGAAAATCAAAAAACCTGACGGGAGTGAGTGTCTACCAGCAGCGCCAGACGGGATTCGGGGCTTCCCCCGGTGC 1360
TGTTAGAACTTTAGTTTTTTGGACTGCCCTCACTCACAGATGGTCGTCGCGGTCTGCCCTAAGCCCCGAAGGGGGCCACG
                .     .     .      .   | |   .       .  | .         ||| |   ||
                                     1317  1325                    1352     1360
                                           1325                    1352     1359
                                           1327                    1353     1360
                                           1328                    1353
                                           1328                    1353
                                                                   1353
                                                                   1354
                                                                   1354
                                                                   1356
                                                                   1356
                                                                   1359

HgiA I              Bsl I
    Bsp1286 I           Sau96 I       BgmA I
    ApaL I              Ava II        Msp I
    Alw21 I             Nla IV        Hpa II         Bsl I   Mnl I      Mbo II
      |                  || |          | |            |       |          |
CGGTATGTGCACAAAGTATCAGGAACGGGACCGTGTGCCGGAGACTTTGCCTTCCATAAAGAGGGTGCTTTCTTCCTGTA 1440
GCCATACACGTGTTTCATAGTCCTTGCCCTGGCACACGGCCTCTGAAACGGAAGGTATTTCTCCCACGAAAGAAGGACAT
      |       .     || *      |  |       .  |        .    *|     .|       .|
    1367                1387         1398                  1414   1421    1431
    1367                1388         1398
    1367                1388         1401
    1367                1391
 Taq I
 Sau3A I
 Mbo I                        Mnl I
 Dpn II                       Sec I
 Dpn I                        BsaJ I             Eco57 I                            Alu I
  | |                          |                   |                                 |
TGATCGACTTGCTTCCACAGTTATCTACCGAGGAACGACTTTCGCTGAAGGTGTCGTTGCATTTCTGATACTGCCCCAAG 1520
ACTAGCTGAACGAAGGTGTCAATAGATGGCTCCTTGCTGAAAGCGACTTCCACAGCAACGTAAAGACTATGACGGGGTTC
  | |         .              ||       .           |             .            |.
 1442                        1468                1485                        1519
 1442                        1468
 1442                        1470
 1444

Bsl I
                                                          Sau96 I
                                                          Nla IV
                                          Msp I           Ava II     Rma I
                  Alu I                   Hpa II          PpuM I     Mae I
         Xmn I    Eco57 I                 Cfr10 I         EcoO109 I
 Dde I   Mbo II                           BsrF I          Mnl I      Bfa I
  | |     || |                             |              |||  |     |
CTAAGAAGGACTTCTTCAGCTCACACCCCTTGAGAGAGCCGGTCAATGCAACGGAGGACCCGTCTAGTGGCTACTATTCT 1600
GATTCTTCCTGAAGAAGTCGAGTGTGGGGAACTCTCTCGGCCAGTTACGTTGCCTCCTGGGCAGATCACCGATGATAAGA
  | |  .  || | .          .         ||.          .      ||| |        .           .
 1521    1533                       1558                1574         1584
         1525   1534                1558                1575         1584
                1538                1559                1575         1584
                                    1559                1576
                                                        1576
                                                        1580
```

PSEUDOTYPED RETROVIRUS WITH MODIFIED EBOLA GLYCOPROTEIN

This application claims the benefit of U.S. Provisional Application Ser. No. 60/386,064, filed 4 Jun. 2002, and of U.S. Provisional Application Ser. No. 60/458,070, filed 27 Mar. 2003, each of which is incorporated herein by reference in its entirety.

FIELD OF THE INVENTION

This invention relates generally to pseudotyped viruses and methods of use of the viruses. Specifically, the invention relates to retroviruses pseudotyped with glycoproteins in which an O-glycosylation region has been modified, and use of these viruses for gene transfer and gene therapy.

BACKGROUND OF THE INVENTION

Gene therapy is one of the fastest growing areas in experimental medicine. However, most studies are only Phase I or Phase II clinical studies designed mainly to evaluate the toxicity of the viral vectors and constructs being used. A major drawback has been the design of vectors that are both safe and efficacious. Recent efforts in the field have been directed toward the use of retroviral vectors and viral vectors pseudotyped with glycoproteins from highly virulent viruses such as filoviruses.

Retroviruses are ribonucleic acid (RNA) viruses that include an RNA genome enclosed within a viral capsid wherein the capsid is surrounded by an envelope, or lipid bilayer. Glycoproteins present in the lipid bilayer interact with receptors on the surface of various host cells and allow the retroviruses to enter the host cell. Once in the cell, the retroviruses reverse transcribe the RNA of the viral genome into a double-stranded DNA and incorporate the DNA into the cellular genome as a provirus. Gene products from the integrated foreign DNA may then be produced so that progeny viral particles may be assembled. As retroviruses can be modified to carry exogenous nucleotide sequences of interest, such recombinant retroviruses have a variety of uses. For example, such recombinant retroviruses are important in introducing desired exogenous sequences into a cell, so that relatively high levels of the protein encoded by the sequences may be produced. However, use of such recombinant retroviruses has several drawbacks.

One such drawback is that retroviruses do not have a broad host range. Efforts at increasing the host range of retroviruses have included substituting the envelope glycoproteins of the retrovirus with that of a different virus, thus forming a pseudotyped retrovirus. The pseudotyped retrovirus advantageously has the host range of the different virus. However, some retroviruses have been pseudotyped with viral glycoproteins that are toxic to cells, so the cells can only produce the virus for a limited time. Furthermore, in many cases, the pseudotyped retroviruses cannot be stably produced and may not be produced at a high titer. Stable cell lines have been developed to overcome the toxicity problems and to stably produce such pseudotyped retroviruses. However, there still exists a need for pseudotyped retroviruses that will allow for the production of high titers that would be required for routine gene transfer and/or gene therapy.

Thus it would be desirable to have a pseudotyped retrovirus that is not toxic to cells and produces high titers of a competent virus. It would also be desirable to have a cell line to produce such retroviruses. Methods for using such a virus would also be desirable.

SUMMARY OF THE INVENTION

It has been discovered that deleting the O-glycosylation region of a viral glycoprotein of a pseudotyped retrovirus allows for stable production of the pseudotyped virus from various cell lines. Pseudotyped retroviruses containing viral glycoproteins with a deleted O-glycosylation region were produced in higher titer than those with wild-type viral glycoproteins, and were also more efficient in transducing target cells. Accordingly, one aspect of the invention provides pseudotyped retroviruses that include recombinant RNA surrounded by, enclosed within, or otherwise associated with a retroviral core that includes a viral capsid, matrix and nucleocapsid. Surrounding the retroviral capsid is a lipid bilayer that includes least one viral glycoprotein disposed therein. The O-glycosylation region of the glycoprotein disposed in the lipid bilayer has been modified through deletion, in whole or in part, or mutation. In one embodiment, the viral glycoprotein is a filoviral glycoprotein such as, but not limited to, Ebola virus or Marburg virus glycoprotein. The recombinant RNA preferably contains a nucleotide sequence that defines a selected biomolecule intended for delivery to the target cell. The nucleotide sequence can encode a protein to be expressed in the target cell, or it can function as a bioactive RNA in the target cell.

In another aspect, the invention provides producer cells for producing pseudotyped retroviruses having a viral glycoprotein in which the O-glycosylation region is deleted, in whole or part. Accordingly, the present invention provides eukaryotic producer cells that include nucleotide sequences encoding retroviral proteins Gag polypeptide, Pro polypeptide, and Pol polypeptide and a fourth nucleotide sequence encoding at least one viral glycoprotein in which the O-glycosylation region of the glycoprotein has been modified. Preferably, the fourth nucleotide sequence encodes a filoviral glycoprotein, such as, for example, a Marburg virus or Ebola virus glycoprotein having a modified O-glycosylation region as described herein. In a preferred form of the invention, the cells stably produce inventive pseudotyped retroviruses.

In a further aspect of the invention, methods for introducing nucleotide sequences into a target cell using the pseudotyped viruses of the present invention are provided. The viruses can be used to introduce a nucleotide sequence into a cell in cell culture, ex vivo or in vivo. The pseudotyped viruses of the invention are useful for introduction of a nucleotide sequence into a wide range of cell types.

In yet another aspect of the invention methods are provided for producing high titers of pseudotyped retroviruses. The methods involve introducing into a recombinant producer cell nucleotide sequences that encode a viral glycoprotein in which the O-glycosylation region is modified. Also present in the cells are nucleotide sequences that encode for other proteins necessary to produce a pseudotyped retrovirus in high titers and that is more efficient in transfecting target cells.

Additional objects, advantages, and features of the present invention will become apparent from the following description, taken in conjunction with the accompanying drawings.

BRIEF DESCRIPTION OF THE DRAWINGS

FIG. 1B shows the nucleotide sequence (SEQ ID NO:2) and restriction map of plasmid pEboGPΔ309-489. The sequence of the modified Ebola glycoprotein begins with the ATG start codon at nucleotides 956-958 and ends with the TAG stop codon at nucleotides 2447-2449. The O-glycosylation region represented by wild-type codons 309-489 has been deleted in this construct. Codon 308 begins at nucleotide 1877 and codon 490 begins at nucleotide 1886. The insertion sequence between codons 308 and 490 (TCTAGA at nucleotides 1880-1886) encodes the dipeptide Ser-Arg.

FIG. 1C shows a portion of the nucleotide sequence (SEQ ID NO:1) and restriction map of plasmid pEboGP showing the complete coding sequence of Ebola glycoprotein. The coding sequence begins with the ATG start codon at nucleotides 956-958 and ends with the TAG stop codon at nucleotides 2984-2986. The O-glycosylation region represented by wild-type codons 309-489, which is deleted in pEboGPΔ309-489, begins at nucleotide 1880 and ends at nucleotide 2422.

DETAILED DESCRIPTION OF ILLUSTRATIVE EMBODIMENTS

Figure 1A:
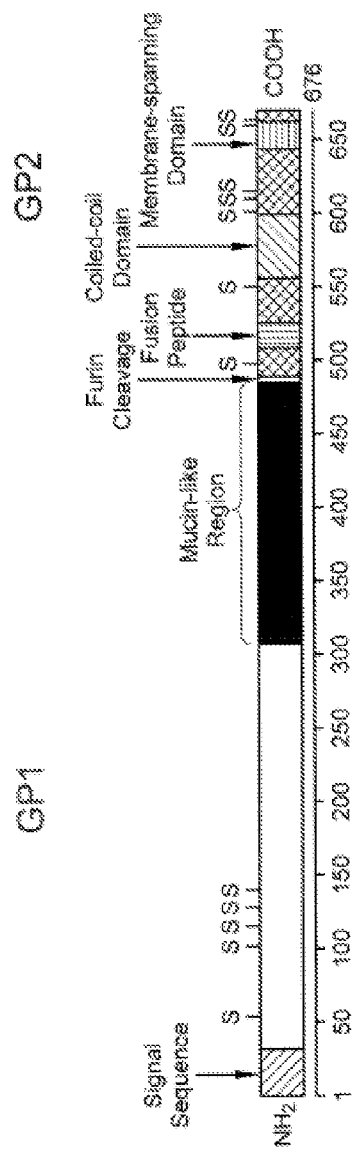
FIG. 1A is schematic representation of the Ebola virus glycoprotein showing the $GP_1$ and $GP_2$ subunits of the glycoprotein drawn to scale with residue numbers indicated below the diagram.

It has been discovered that deleting the O-glycosylation region of a viral glycoprotein of a pseudotyped retrovirus allows for stable production of the pseudotyped virus from producer cell lines. Pseudotyped viruses having viral glycoproteins with a deleted O-glycosylation region were produced in higher titer than those with wild-type viral glycoproteins and were also more efficient in transducing target cells.

Accordingly, one aspect of the invention provides a pseudotyped retrovirus. The pseudotyped retrovirus is formed from retroviral components that include a retroviral core surrounded by a lipid bilayer, and a recombinant RNA. Disposed in the lipid bilayer is at least one non-wild-type viral glycoprotein which contains a modified O-glycosylation region. The modification can take the form of a deletion of the O-glycosylation region from the viral glycoprotein, in whole or in part, or mutation of the O-glycosylation region. The resulting pseudotyped retrovirus exhibits increased transduction capacity and expanded tropism, compared to the wild-type retrovirus.

In one embodiment, the viral glycoprotein is a filoviral glycoprotein such as, but not limited to, Ebola virus or Marburg virus glycoprotein.

It has been discovered that eukaryotic producer cells may be constructed that stably produce pseudotyped retroviruses having a viral glycoprotein disposed in their lipid bilayer wherein the O-glycosylation region of the viral glycoprotein has been modified. Modification of the O-glycosylation region results in enhanced glycoprotein processing and incorporation into retroviral particles, allowing for stable production of the pseudotyped viruses.

It has further been discovered that levels of viral transduction into target cells are significantly higher for the pseudotyped retroviruses having glycoproteins with modified O-glycosylation regions as compared to pseudotyped retroviruses bearing wild-type glycoproteins.

Glycoprotein for Use in Retroviral Pseudotyping

The present invention contemplates that the O-glycosylation region of the glycoprotein used to pseudotype the retrovirus is modified, either by deletion (in whole or part) or mutation. Deletion of the O-glycosylation region allows the pseudotyped retrovirus to be stably produced in the recombinant virus producer cells. By "stable production" or "stably produced", it is meant that the producer cells will produce pseudotyped retroviruses indefinitely (i.e., during the life span of the cell). While not wishing to be bound by theory, it is thought that deletion of the O-glycosylation region allows for increased expression of processed glycoprotein in the recombinant virus producer cell. This glycosylation step may be rate limiting during production of the virus, and glycosylation of high amounts of viral glycoproteins may be toxic to the producer cells. Thus, increased expression may be a result of bypassing the post-translation glycosylation step. Increased transduction is observed and may be due to the greater quantity of virus produced.

The viral glycoprotein used in pseudotyping the retrovirus of the invention may be any viral glycoprotein having an O-glycosylation region. An O-glycosylation region can be identified as one that is rich in proline, serine and threonine residues. Such regions can be discovered by searching protein databases for potential O-glycosylation regions using computer algorithms such as NetOGlyc v. 2.0 (J. E. Hansen et al., Glycogonjugate J., 15:115-130, 1998; J. E. Hansen et al., Nucleic Acids Research, 25, 278-282, 1997; J. E. Hansen et al. Biochemical Journal, 308, 801-813, 1995). Alternatively, O-glycosylation regions can be identified biochemically, for example by using antibodies to perform western blots.

Filoviral proteins, such as those of Ebola virus (e.g., Ebola Zaire [complete genome, GenBank Acc. No. NC 002549; glycoprotein, GenBank Acc. No. U23187], Ebola Reston [complete genome, GenBank Acc. No. NC 004161; glycoprotein, GenBank Acc. No. U23152] and Ebola Sudan [glycoprotein, GenBank Acc. No. U23069]; see FIG. 1) and Marburg virus [complete genome, GenBank Acc. No. NC 001608; glycoprotein, GenBank Acc. No. Z12132]), have O-glycosylation regions and infect a broad spectrum of mammalian hosts. By way of non-limiting example, the O-glycosylation region for the Ebola glycoprotein (Zaire) is from about codon 309 to codon 489 of SEQ ID NO:1. The nucleotide sequences encoding the filoviral glycoproteins may be obtained as described in Sanchez et al. (1993) *Virus Res.* 29 (3):215-240 and Will et al., (1993) *J. Virol.* 67:1203-1210. It is expected that other viruses not specifically mentioned herein and having glycoproteins of similar structure to the filoviral glycoproteins may be advantageously used in the present invention.

Viral glycoproteins from filoviruses facilitate the introduction of genes into many different cell types and are therefore preferred for use in the invention. As an example, Ebola glycoprotein-pseudotyped lentiviruses have specificity in particular for transducing airway epithelia cells from the apical surface and therefore hold promise for reagents for gene therapy for diseases of the lung such as cystic fibrosis.

It will be appreciated by the skilled artisan that the O-glycosylation region can be modified by deleting it either in whole or part from the glycoprotein. Deletion involves removing part or all of the nucleotide sequence encoding the region. In embodiments wherein only part of the O-glycosylation region is deleted, a sufficient number of nucleotides is deleted to cause the transduction level in a target cell to increase by at least 2-fold, preferably at least 5-fold, and more preferably at least 10-fold, 20-fold, 50-fold or 100-fold. Transduction levels can be readily determined by using the assay described in Example I.

Alternatively, the nucleotide sequence can mutated, for example by modifying it to replace the codons for serine and threonine, the amino acids that are O-glycosylated, with codons for conservative amino acid substitutions such as alanine which will not be O-glycosylated. A sufficient number of serine and/or threonine residues are mutated such that transduction level into a target cell is increased as described above.

Retroviral Particle

The pseudotyped retrovirus of the invention is a recombinant retroviral particle that includes recombinant RNA surrounded by, enclosed within, or otherwise associated with a retroviral core that includes a viral capsid, matrix and nucleocapsid. A viral glycoprotein, modified to delete or mutate the O-glycosylation region, is disposed within a lipid bilayer which surrounds the retroviral core.

The recombinant RNA includes both coding and noncoding retroviral control elements. The term "nucleotide sequence", or "nucleic acid sequence" as used herein is intended to refer to a natural or synthetic linear and sequential array of nucleotides and/or nucleosides, and derivatives thereof. The terms "encoding" and "coding" refer to the process by which a nucleotide sequence, through the mechanisms of transcription and translation, provides the information to a cell from which a series of amino acids can be assembled into a specific amino acid sequence to produce a polypeptide.

Nucleotide sequences required for retroviral transcription, reverse transcription and integration in the target cell are thus included in the recombinant RNA, as well as elements required for incorporation (packaging) of the retrovirus particle (e.g., psi). Reverse transcriptase and integrase give the retrovirus the ability to incorporate a gene encoding a desired protein into a genome of a target cell after the retrovirus contacts, or is incubated with, the cell. The pseudotyped retrovirus may include other proteins, in addition to integrase, that aid its stable integration into the chromosomes of a target cell. For example, with respect to a lentivirus, the pseudotyped retrovirus may include proteins such as vpr, vif and vpu. Other sequences known to the art that are useful for transducing genes may also be present in the recombinant RNA.

An illustrative, nonlimiting example of the structural organization of a recombinant RNA forming a part of the pseudotyped virus of the invention is a nucleotide sequence that begins with an optional 5' long terminal repeat (LTR) or other transcription and/or integration element(s), followed by a primer binding site (PBS) that initiates reverse transcriptase binding, followed by a viral packaging sequence such as psi, which packaging sequence is optionally flanked by splice acceptor and splice donor sites, followed by a reverse transcriptase initiation site for the second strand, followed by an optional 3' LTR. When the recombinant RNA includes a nucleotide sequence that encodes a desired protein or a bioactive RNA (see below), that sequence is typically located between the splice donor site and the reverse transcriptase initiation site.

The pseudotyped retrovirus of the invention can be replicative or nonreplicative. In most applications, it is desirable that the retrovirus be nonreplicative. Replication incompetent retroviruses typically typically lack one or more of the Gag, Pol, Pro or Env proteins.

The recombinant RNA further optionally includes a nucleotide sequence that defines a selected biomolecule intended for delivery to the target cell. The nucleotide sequence can encode a protein to be expressed in the target cell, or it can function as a bioactive RNA in the target cell. This protein or RNA is produced by a target cell upon introduction of the pseudotyped retrovirus into the target cell. The protein (or RNA) can serve as a detectable marker, or can provide a beneficial or therapeutic effect if introduced into an animal, as described in more detail below.

Recombinant Virus Producer Cells

The invention provides recombinant virus producer cells, preferably eukaryotic cells forming eukaryotic cell lines, that contain nucleotide sequences encoding retroviral Gag polypeptide, retroviral Pro polypeptide, retroviral Pol polypeptide and at least one viral glycoprotein, such as a filoviral glycoprotein, in which the O-glycosylation region of the glycoprotein has been deleted or modified, as described above. (Note that pro and pol often occur so close together on a viral genome that the term pol is often used to refer to both pro and pol). The eukaryotic cell line is grown in vitro to produce the pseudotyped retroviruses.

Any of a wide variety of cells can be selected for in vitro production of a pseudotyped retrovirus according to the invention. Eukaryotic cells are preferred, particularly mammalian cells including human, simian, canine, feline, equine and rodent cells. Human cells are most preferred. It is further preferred that the cell be able to reproduce indefinitely, and is therefore immortal. Examples of cells that may be advantageously used in the present invention include NIH 3T3 cells, COS cells, Madin-Darby canine kidney cells, human embryonic 293T cells and any cells derived from such cells, such as gpnlslacZ ϕNX cells, which are derived from 293T cells and described in the Examples. Highly transfectable cells, such as human embryonic kidney 293T cells, are preferred. By "highly transfectable" it is meant that at least about 50%, more preferably at least about 70% and most preferably at least about 80% of the cells can express the genes of the introduced DNA.

The retroviral gag, pro and pol nucleotide sequences and other retroviral nucleotide sequences needed for forming the specified pseudotyped retroviruses may be obtained from a wide variety of genera in the family Retroviridae, including, for example, Alpharetrovirus (e.g., avian leukosis virus), Betaretrovirus (e.g., mouse mammary tumor virus), Gammaretrovirus (e.g., murine leukemia virus and Moloney monkey leukemia virus [Mo-MuLV]), Deltaretrovirus (e.g., bovine leukemia virus), Epsilonretrovirus (walleye dermal sarcoma virus), Lentivirus (e.g., humanimmunodeficiency virus I, feline immunodeficiency virus and Chimpanzee foamy virus) and spumavirus. Retroviral sequences are preferably obtained from the Moloney murine leukemia virus (Mo-MuLV). Such sequences are well known in the art. For example, nucleotide sequences encoding MMLV Gag, Pro and Pol polypeptides may be found in Shinnick et al., *Nature,* 293:543-548 (1981).

Depending on the application, the retroviral components of the pseudotyped retrovirus of the invention are preferably derived from a simple retrovirus such as MoMuLV, or a more complicated retrovirus such as a lentivirus. Examples of lentiviruses include feline immunodeficiency virus (FIV), human immunodeficiency virus (HIV), simian immunodeficiency virus (SIV) and equine infectious anemia virus (EIAV). Unlike most other retroviruses, lentiviruses have the capacity to integrate the genetic material they carry into the chromosomes of non-dividing cells as well as dividing cells. Therefore, lentiviral nucleotide sequences encoding proteins that allow for chromosomal integration of virally transported nucleic acid in non-dividing cells are advantageously employed, as the host range of the pseudotyped retroviruses will be broadened.

Suitable retroviruses, including those described above, are readily publicly available from the American Type Culture Collection (ATCC) and the desired nucleotide sequences may be obtained from these retroviruses by methods known to the skilled artisan. For example, the nucleotide sequences may be obtained by recombinant DNA technology. Briefly, viral DNA libraries may be constructed and the nucleotide sequences may be obtained by standard nucleic acid hybridization or polymerase chain reaction (PCR) procedures, using appropriate probes or primers. Alternatively, supernatant medium from cells infected with the respective virus can be isolated and the desired retroviral nucleotide sequences may be amplified by PCR. Such vectors may also be constructed by other methods known to the art.

It is preferred that the gag, pro and pol nucleotide sequences are contiguous to each other as found in native retroviral genomes, such as in the order 5'-gag-pro-pol-3'. It is further preferred that these retroviral nucleotide sequences are chromosomally-integrated into the cellular genome of the producer cell. Furthermore, the gag-pro-pol nucleotide sequences are preferably operably linked at the 5' end of the gag nucleotide sequence to a promoter sequence, so that transcription of the sequences may be achieved.

A nucleic acid sequence is "operably linked" to another nucleic acid sequence, such as a promoter sequence, when it is placed in a specific functional relationship with the other nucleic acid sequence. The functional relationship between a promoter and a desired nucleic acid typically involves the nucleic acid and the promoter sequences being contiguous such that transcription of the nucleic acid sequence will be facilitated. Two nucleic acid sequences are further said to be operably linked if the nature of the linkage between the two sequences does not interfere with the ability of the promoter region sequence to direct the transcription of the desired nucleotide sequence, or interfere with the ability of the desired nucleotide sequence to be transcribed by the promoter sequence region. Typically, the promoter element is generally upstream (i.e., at the 5' end) of the nucleic acid coding sequence.

A wide variety of promoters are known in the art, including cell-specific promoters, inducible promoters, and constitutive promoters. The promoters may further be selected such that they require activation by activating elements known in the art, so that production of the protein encoded by the specified nucleic acid sequence may be regulated as desired. It is well within the purview of a person skilled in the art to select and use an appropriate promoter in accordance with the present invention. For example, the promoters that may be advantageously present in the cell, 5' to the gag-pro-pol sequences, include the rat actin promoter and the MMLV promoter. Furthermore, the cytomegalovirus (CMV) promoter has been found to be an excellent promoter in the inventive system.

Other regulatory elements, such as enhancer sequences, cooperate with the promoter and transcriptional start site to achieve transcription of the nucleic acid insert coding sequence, may also be present in the cell 5' to the nucleotide sequences that encode retroviral proteins. By "enhancer" is meant nucleotide sequence elements which can stimulate promoter activity in a cell, such as a bacterial or eukaryotic host cell.

Another aspect of the invention provides methods of making eukaryotic cells for producing pseudotyped retroviruses. The method includes introducing into the cells described above the nucleotide sequences described above, i.e., those encoding the retroviral Gag, Pro and Pol polypeptides, and those encoding a filoviral glycoprotein in which the O-glycosylation region is deleted or mutated, in part or in whole, into the cell.

The nucleotide sequences may be introduced into the desired cell utilizing any of variety of vectors known to the skilled artisan. For example, plasmid vectors, cosmid vectors, and other viral vectors, such as retroviral vectors, may be used. It is preferred that the nucleotide sequences encoding the Gag, Pro and Pol polypeptides are on a vector separate from the nucleotide sequences encoding the viral glycoproteins.

In one mode of practicing the invention, plasmid vectors are advantageously used to introduce, or transfect, the nucleotide sequences into the selected cell. A wide variety of plasmid vectors may be used, including pTRE, pCMV-Script and pcDNA3, although pcDNA3 is a preferred vector. The gag, pro and pol nucleotide sequences are preferably on the same plasmid, and, as discussed above, are preferably contiguous to each other. However, the skilled artisan is aware that other spatial configurations of the nucleotide sequences may be utilized when constructing the plasmids. The vector also preferably includes a promoter 5' to, or upstream from, the gag nucleotide sequence. The vectors may further include other regulatory elements, such as enhancer sequences, as discussed above.

The nucleotide sequences encoding the viral glycoproteins are preferably, but need not be, on a plasmid, or other vector, separate from the gag, pro and pol nucleotide sequences. The viral glycoprotein encoding sequences, such as the sequences encoding the filoviral glycoproteins are also preferably operably linked to a promoter sequence described above. In the case of viral glycoproteins that are formed from separate polypeptides, the two polypeptides may, if desired, be supplied on different plasmids. It is preferred, however, that such sequences are on the same vector, and preferably contiguous to each other so they will be transcribed utilizing the same promoter. In one preferred form of the invention, the promoter sequence is a cytomegalovirus promoter sequence. Plasmids, or other vectors carrying the nucleotide sequences encoding the viral glycoproteins, may also include other regulatory elements, such as enhancers, as described above.

The vectors may be introduced into the cells in a variety of ways known to the skilled artisan, for example, discussed in *Current Protocols in Molecular Biology*, John Wiley and Sons, edited by Ausubel et al. (1988) and Sambrook et al., *Molecular Cloning, A Laboratory Manual*, Cold Spring Harbor Laboratory Press (2000). For example, vectors may be transfected into a cell by a calcium phosphate precipitation method. Other methods for introduction of the vectors include, for example, electroporation and lipofection.

In order for the producer cells to produce the pseudotyped retroviruses of the invention, they must express the recombinant RNA that is ultimately packaged into the retroviral particles. The producer cells must therefore be supplied with the recombinant RNA. The recombinant RNA may be introduced into the producer cell as DNA or as RNA, in any of a variety of ways known to the skilled artisan. Plasmids are typically used to introduce DNA encoding the recombinant RNA into the producer cells. Alternatively, defective retroviruses (i.e., those which do not have the capability to produce all of the viral proteins necessary for production of a retrovirus having the ability to infect a cell and produce progeny viruses) can be utilized to cause genomic integration of the DNA encoding the recombinant RNA into the producer cell's genome.

Pseudotyped Retrovirus as a Vehicle for Delivery of Genetic Material

In many cases, one may wish to quickly visually detect those cells which have taken up a vector and that produce a specified protein from the vector. The desired protein encoded by the retroviral recombinant RNA may accordingly be one that facilitates detection of entry of the pseudotyped retrovirus into a target cell. The desired protein may be, for example, a visually detectable component, or marker, such as one that emits visible wavelengths of light, or one that can be reacted with a substrate to produce color of specified wavelengths or other detectable reaction. For example, such nucleotide sequences include the nucleotide sequence encoding the fluorescent proteins such as green, blue and red fluorescent proteins (e.g., *A. victoria* green fluorescent protein (GFP); nucleotide sequences listed in Prasher et al., *Gene* 111:229 (1992)) and the LacZ gene (produces β-galactosidase, which reacts with a well-known substrate, X-gal), both of which are well known in the art and may be obtained commercially. Cells that have taken up the vector and express the nucleotide sequences encoding a protein may be identified and separated from cells that do not express the sequences by a fluorescence-activated cell sorting procedure as known in the art.

The invention further provides a screening kit for use in evaluating transduction efficiency of a retrovirus in selected target cells. The screening kit includes a pseudotyped retrovirus of the invention, appropriate buffers, and instructions for use.

Advantageously, expression of a detectable marker allows viral entry into a target cell to be confirmed. Expression of the detectable marker can also be used to ensure that the pseudotyped retroviruses that are formed are replication incompetent (i.e., do not have all the sequences necessary in their viral genome to produce progeny retroviruses). Supernatant isolated from target cells transduced by the pseudotyped retroviruses and contacted with a second target test cell should not result in localization of the fluorescent protein in the second target test cell because there should be no retroviruses in the supernatant. A lack of retroviruses in the supernatant would indicate that no replication competent viruses are produced inside the initial target cell, so none of those initial target cells serves as a source of competent retroviruses. Even though it does not make new virus particles, the initial target cell nonetheless expresses the marker because the marker is introduced into its genome via the pseudotyped retrovirus with which it was transduced.

In addition or alternatively to the detectable marker, the pseudotyped retroviruses of the invention may include recombinant RNA that operably encodes a protein that is needed by an animal, either because the protein is no longer produced, is produced in insufficient quantities to be effective in performing its function, or is mutated such that it either no longer functions or is only partially active for its intended function. Other examples of nucleotide sequences that can be included in the retroviral recombinant RNA include those that encode a protein or bioactive RNA (typically a ribozyme) that is effective to treat a viral infection, stimulate the hosts immune system, or preferentially infect and kill cancer cells in the host.

The present invention further includes methods of introducing desired nucleotide sequences into a target cell using a pseudotyped retrovirus. A target cell is eukaryotic and can be a vertebrate or invertebrate cell. Examples of eukaryotic cells include cells from insects, birds, fish and mammals. Preferably the target cell is a mammalian cell, more preferably a feline, canine, bovine, or human cell. The mammalian cell can be a normal cell or a transformed, cancerous or precancerous cell. The target cell may be a cell already infected by a virus.

In one embodiment, the method of delivering the nucleotide sequences to the target cell includes contacting, or transducing, a target cell permissive for filoviral entry, with a retrovirus that has been pseudotyped with a filoviral glycoprotein as described above that includes the desired nucleotide sequence in its genome. The cells can be contacted while present in the organism (in vivo) (Sharkey et al., *J Virol*, 75:2653-2659 (2001)), while explanted and outside the organism (ex vivo), or in cell culture (Sinn et al., *J Virol* 2003 May 15; 77(10):5902-10 and Kang et al., *J. Virol.*, 76:9378-9388 (2002)). Cells contacted ex vivo can, if desired, be reimplanted into the organism. In vivo delivery of the pseudotyped retrovirus can be accomplished using methods well known to the art of therapeutic delivery of genetic material, such as injection, perfusion, aerosolization followed by inhalation, and the like. Dosages can be readily determined by reference to existing retroviral gene therapies.

When the nucleotide sequence encodes a desired protein, the target cell is selected so that it allows expression of the selected nucleotide sequence. The level of transduction may be determined by assay methods known to the skilled artisan, and include assaying for the protein of interest encoded by the introduced nucleotide sequences or assaying for the presence of the nucleotide sequences.

Any existing retroviral therapy can be modified according to the invention by including in the lipid bilayer of the retrovirus the modified glycoproteins described herein. Pseudotyping with the modified glycoproteins increases the efficiency of gene therapy because the transduction levels are significantly increased, making the procedure more economical as well.

Reference will now be made to specific examples illustrating the compositions and methods above. It is to be understood that the examples are provided to illustrate preferred embodiments and that no limitation to the scope of the invention in intended thereby.

Example I

Murine Leukemia Virus Pseudotyped with Ebola Glycoprotein Lacking O-Glycosylation Region Materials and Methods Cell lines and culture conditions. The human kidney cell line 293 (ATCC Number CRL-1573), the mouse embryo cell line NIH 3T3 (CRL-1658), and the 293T-derived φNX (second generation retroviral packaging cells) (Grignani et al., *Cancer Res*, 58:14-19 (1998); Pear et al., *Proc. Natl. Acad. Sci. USA*, 90:8392-8396 (1993); Swift et al., p. 10.17.14-10.17.29. In R. Coico (ed.), Current Protocols in Immunology supp. 31. J. Wiley & Sons (1999)) and gpnlslacZ cell lines were cultured in Dulbecco's minimal essential medium (DMEM) containing 10% heat inactivated fetal bovine serum, 2 mM glutamine, 100 units Penicillin G, and 100 µg/ml streptomycin sulfate, with or without 0.25 µg/ml amphotericin B (growth medium). The gpnlslacZ cells produce envelope protein-deficient replication-incompetent Mo-MuLV particles carrying MFG.S-nlslacZ, a retroviral vector encoding a nuclear localizing β-galactosidase (Sharkey et al., *J Virol*, 75:2653-2659 (2001)).

Plasmids and site-directed mutagenesis. A modified version of the plasmid pTM1 was used in transient expression studies of GP sequences using a vaccinia virus-T7 RNA polymerase (VV-T7) system (Elroy-Stein et al., *Proc Natl Acad Sci USA*, 86:6126-6130 (1989)). The pTM1 vector was modified to remove an ATG codon (within an NcoI site) at the beginning of the multiple cloning site by NcoI digestion, mungbean nuclease treatment, and ligation of the blunt-ended DNA. This vector, pTM1(ΔNcoI), was used to subclone the entire Ebola virus GP open reading frame (ORF). The GP ORF was cleaved from the plasmid pGEM-EMGP1 (Sanchez et al., *Virus Res*, 29:215-240 (1993)) by digestion with BamHI and DraI, and the fragment isolated and directionally ligated into the pTM1(ΔNcoI) vector cleaved with BamHI and StuI. The resulting clone, pTM1(ΔNcoI)-GP, was used as the target DNA for all site-directed mutagenesis reactions. This clone encodes a GP sequence that differs from the wild-type amino acid sequence in a single residue within the membrane spanning sequence (I662V), and for comparative purposes will be referred to as "wild-type sequence". This mutation is present in the original pGEM3Zf(−)-GP clone, but does not appear to affect the processing or function of the GP. GP residue numbering commences with the methionine of the signal sequence and is continuous through the $GP_1$ and $GP_2$ sequences.

Figure 1B:
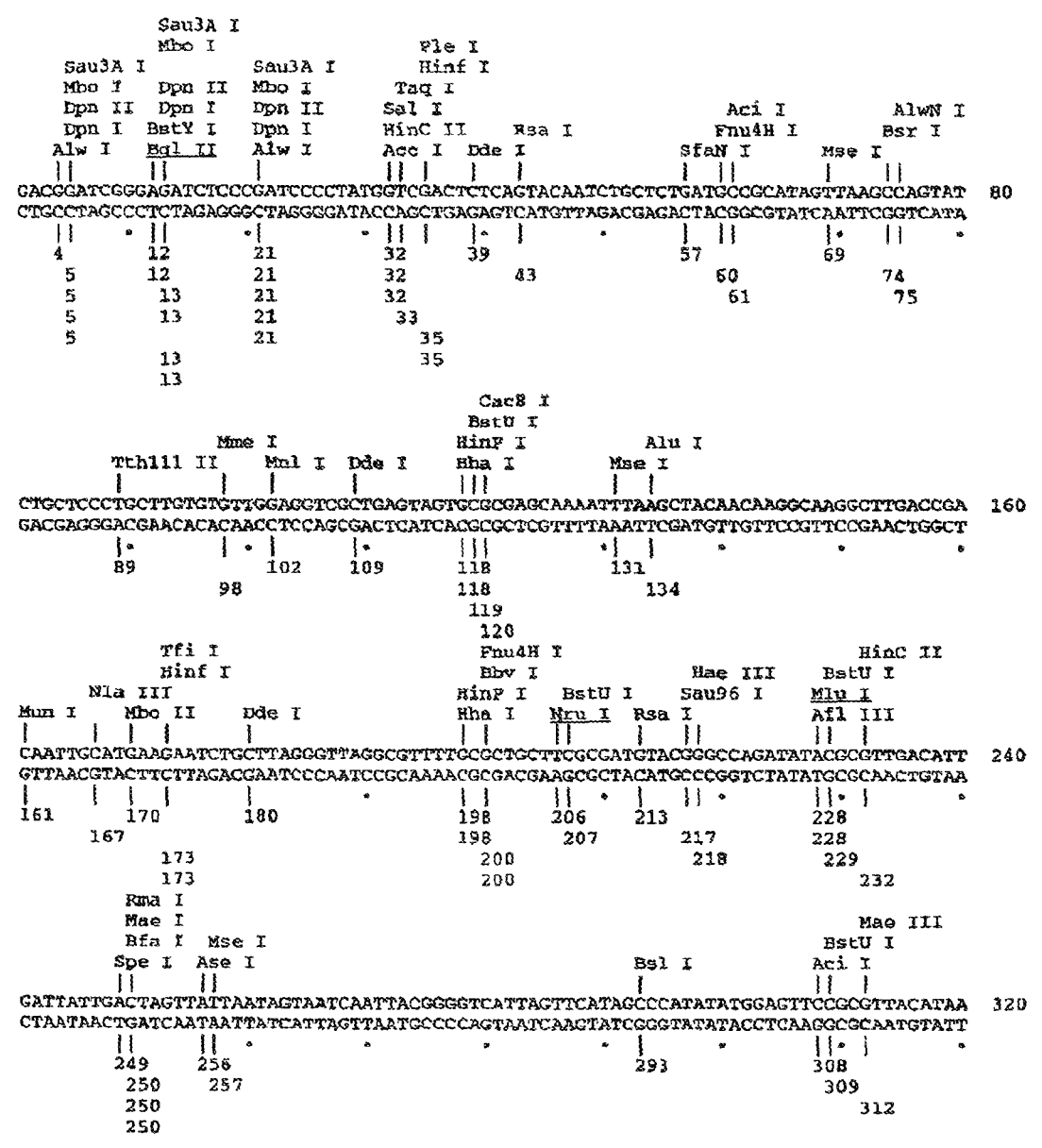
Figure 1B:
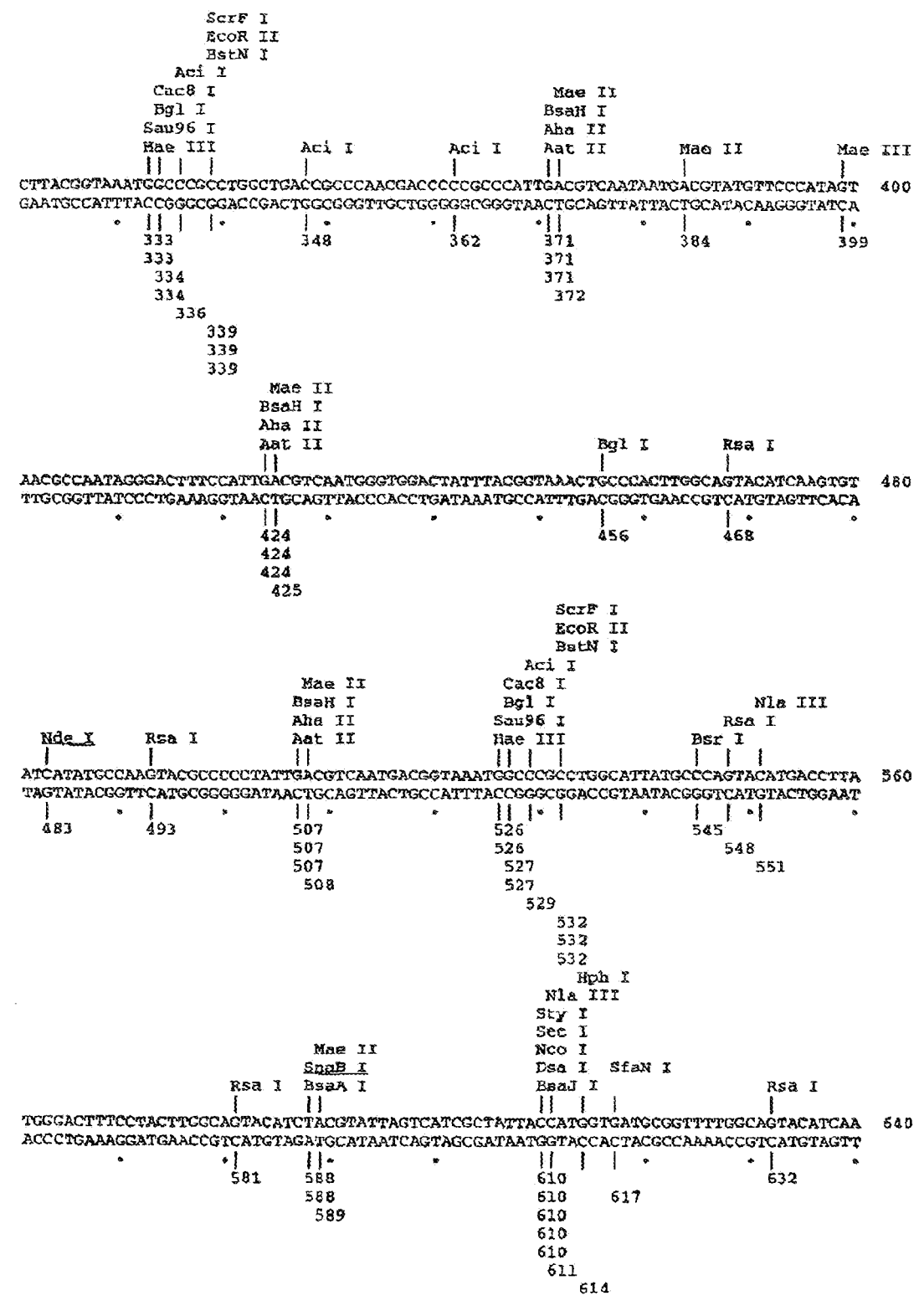
Figure 1B:
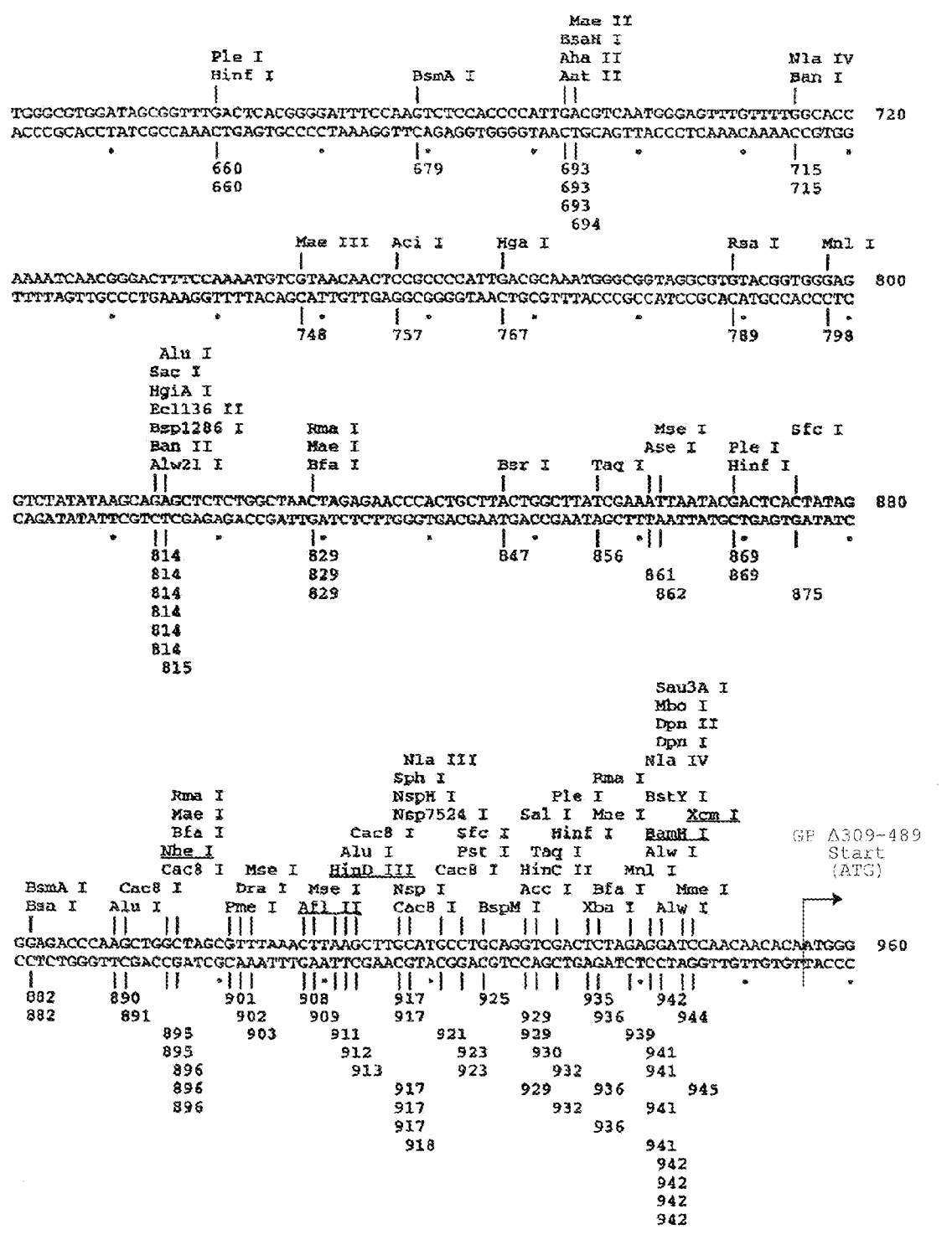
Figure 1B:
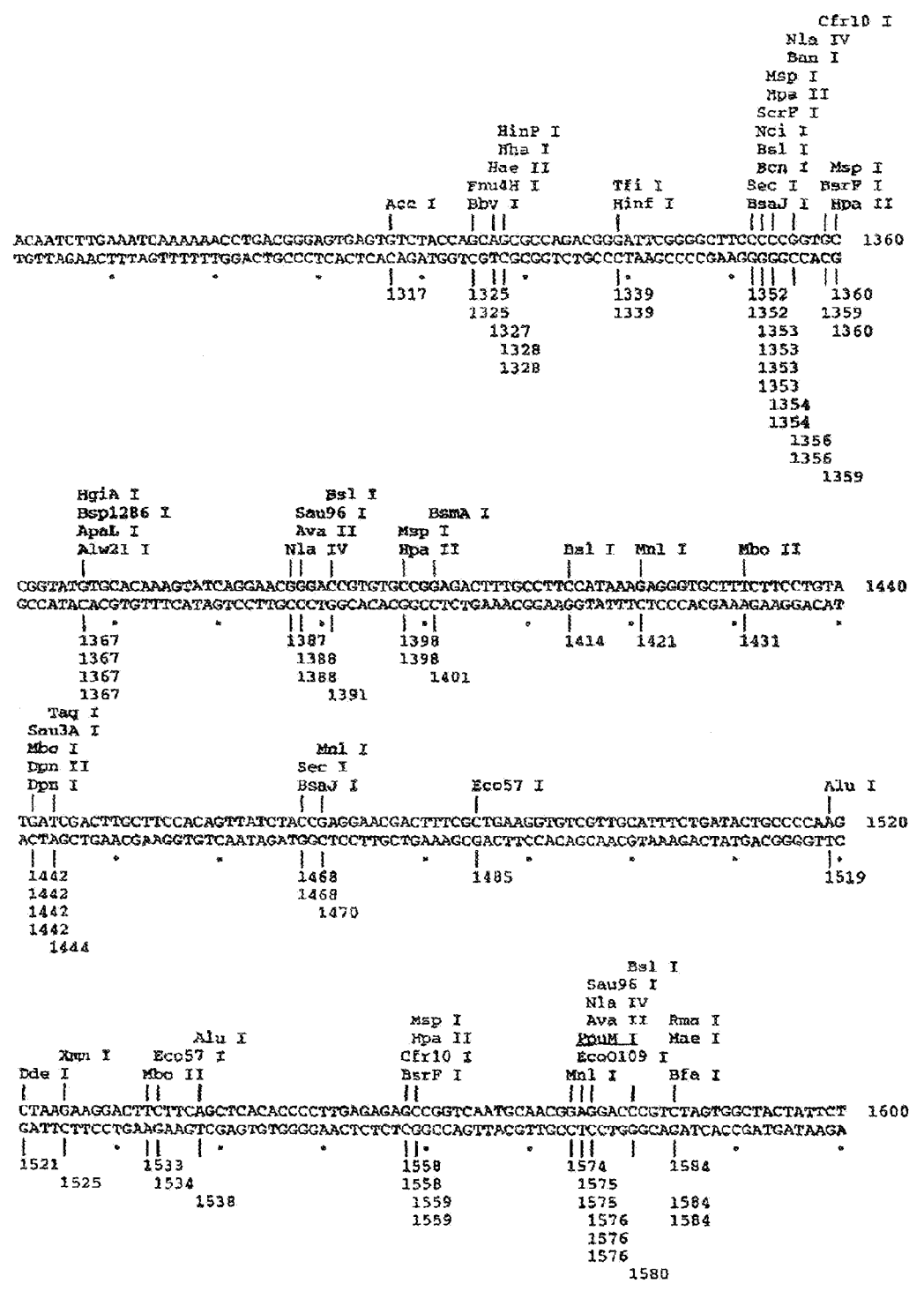
Figure 1B:
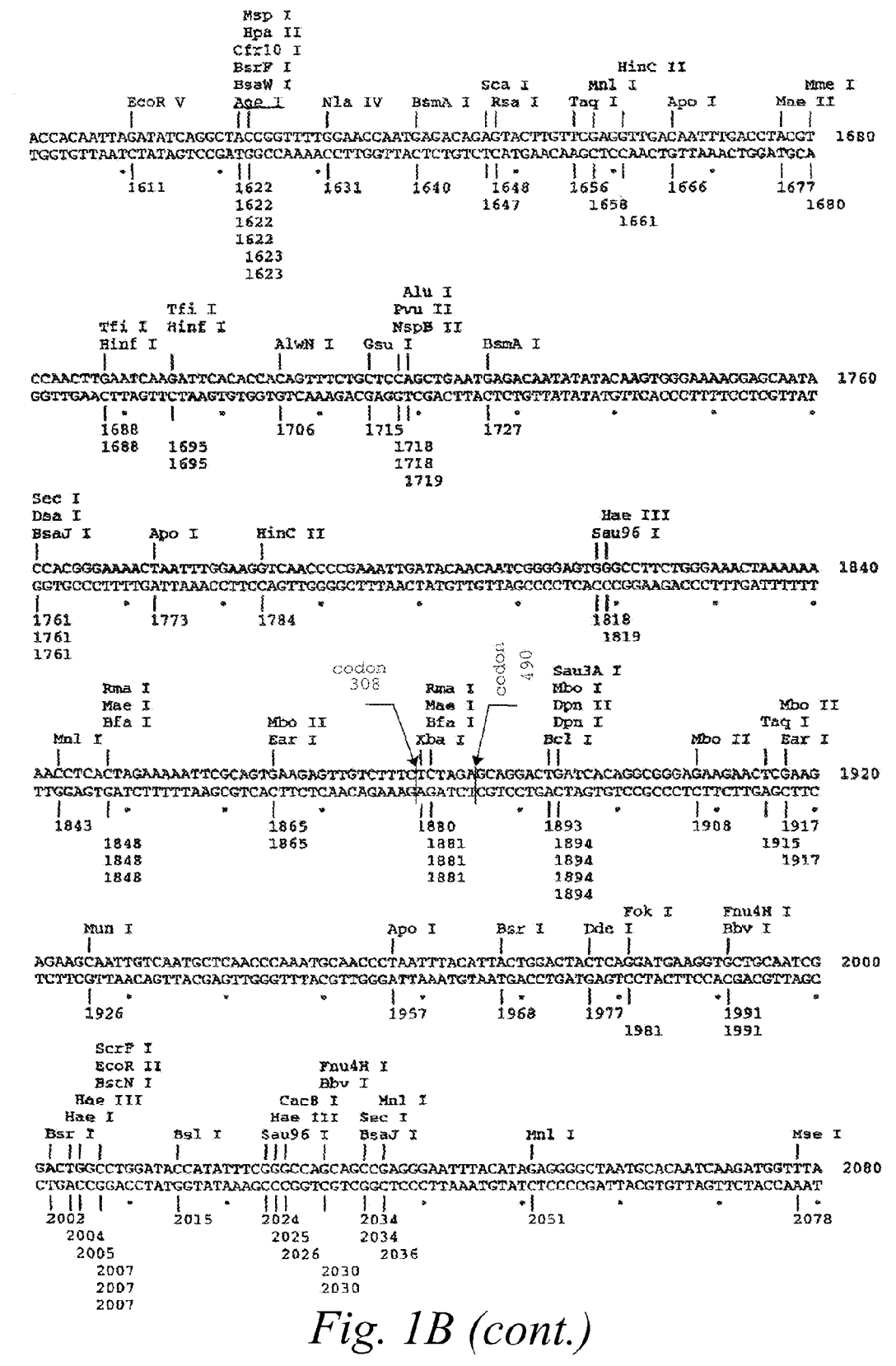
Figure 1B:
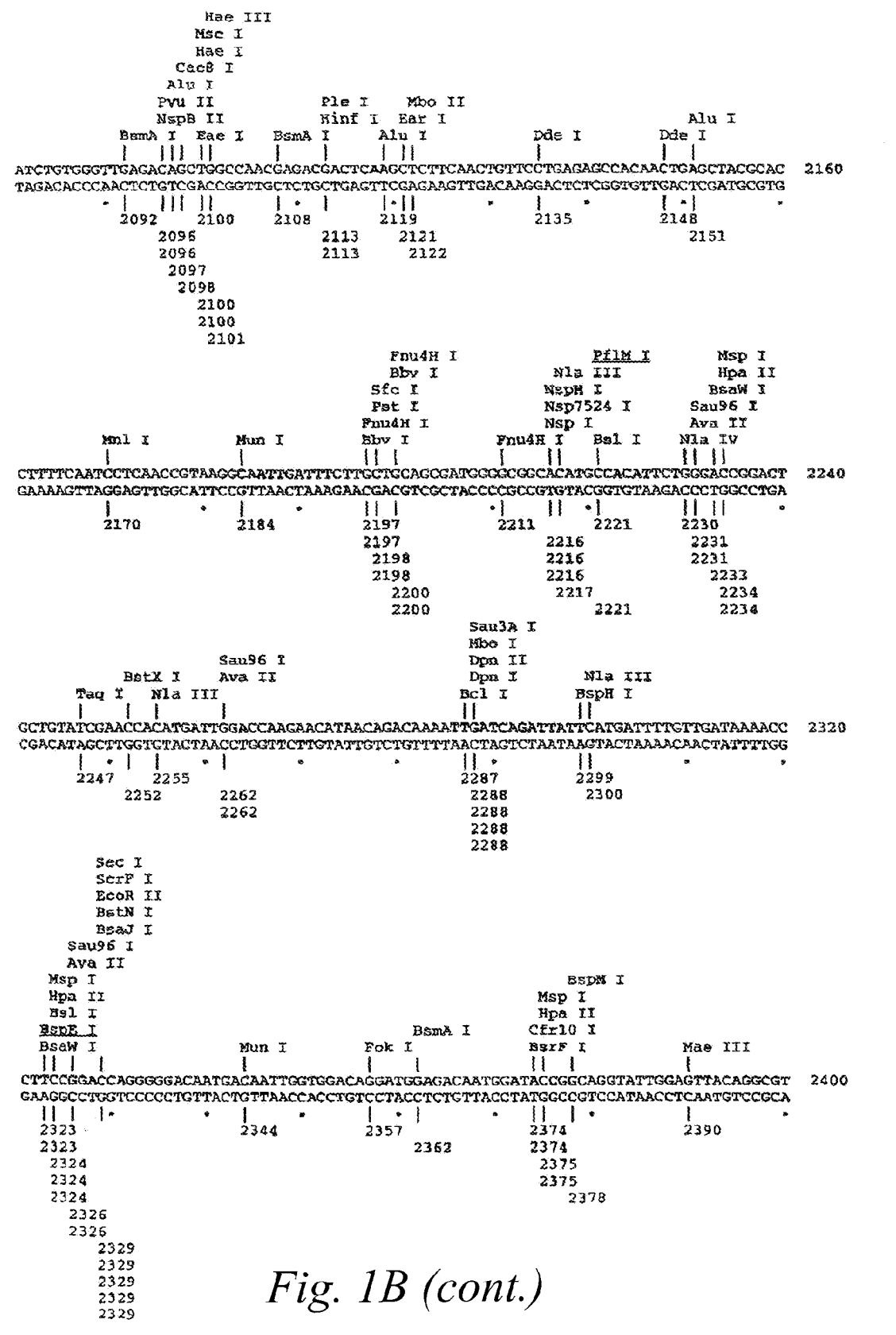
Figure 1B:
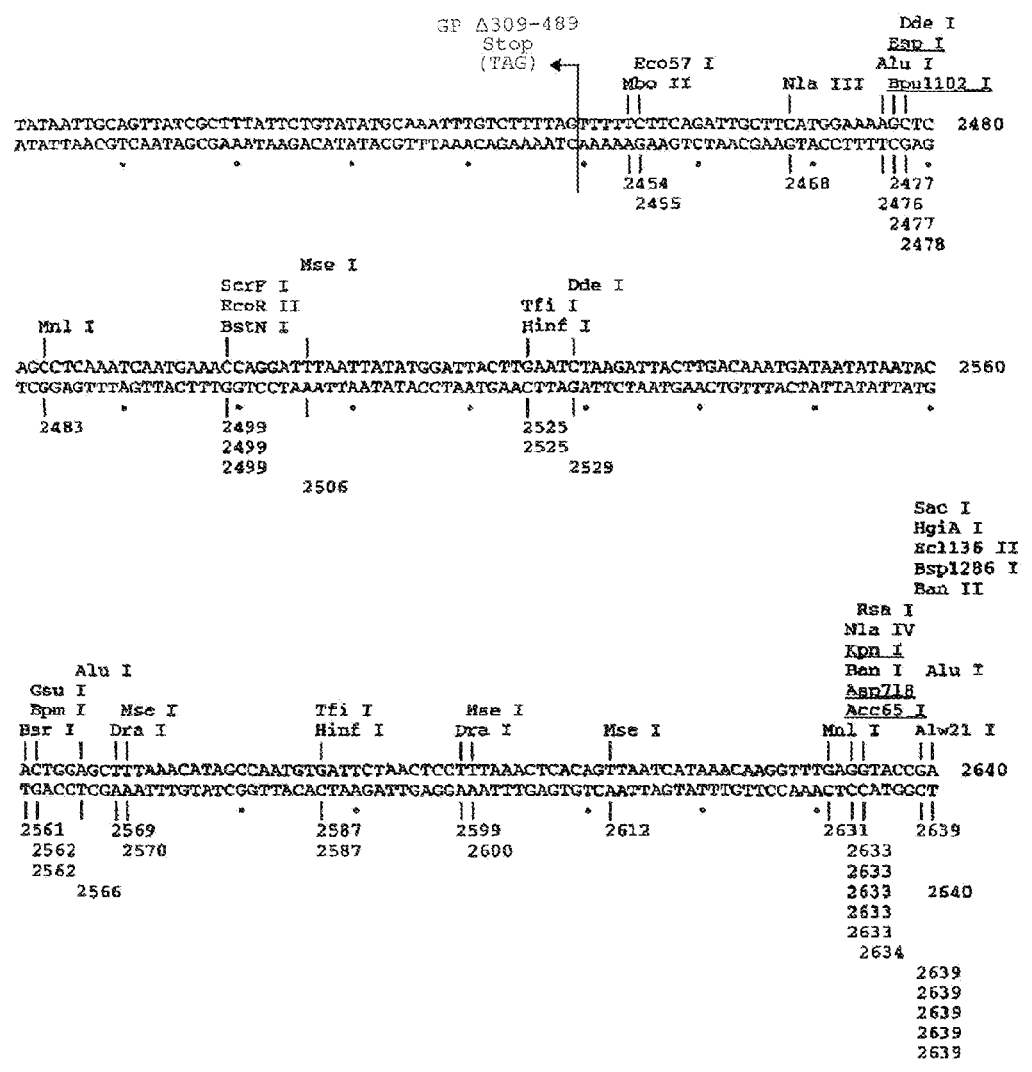
Figure 1B:
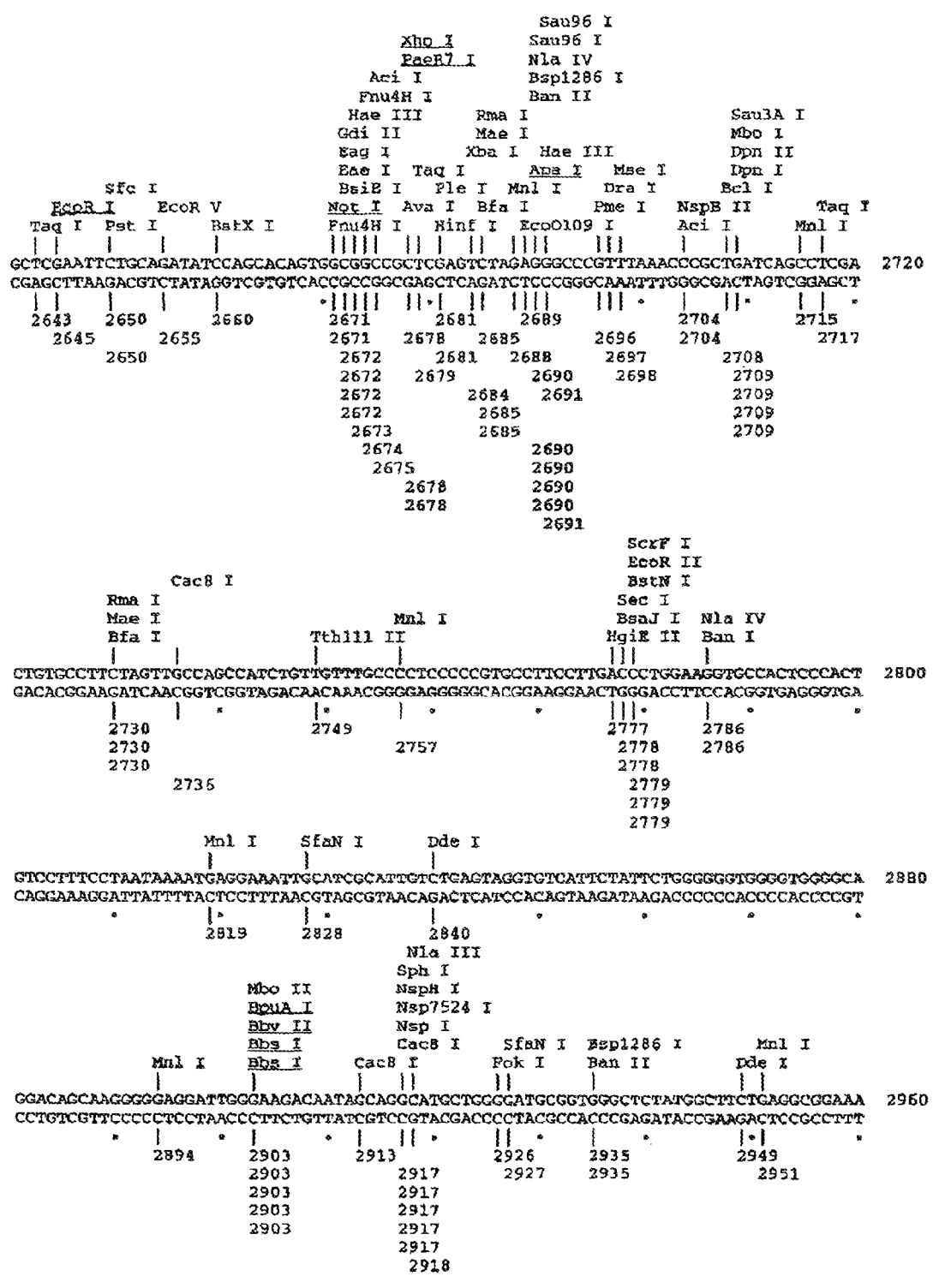
Figure 1B:
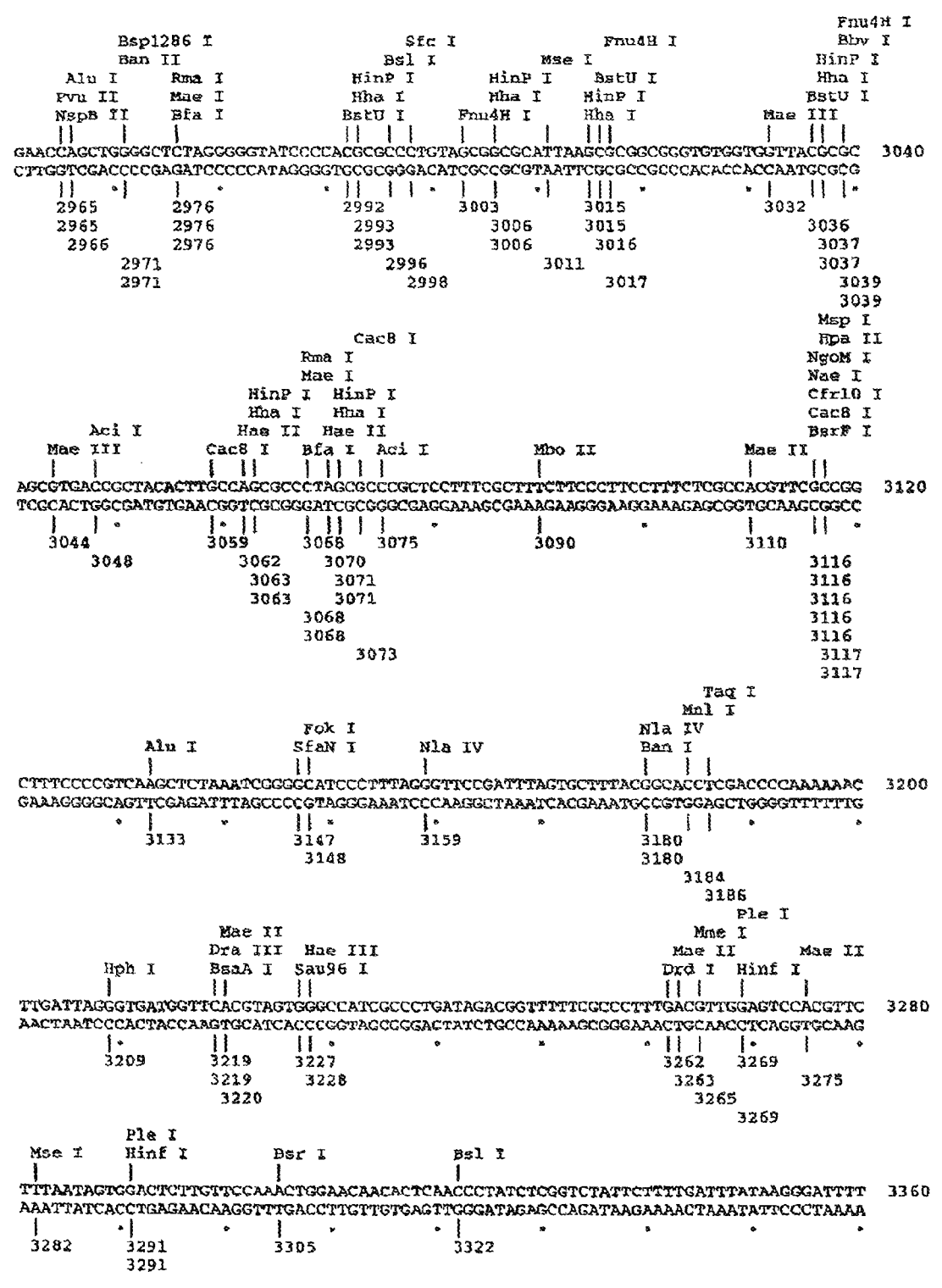
Figure 1B:
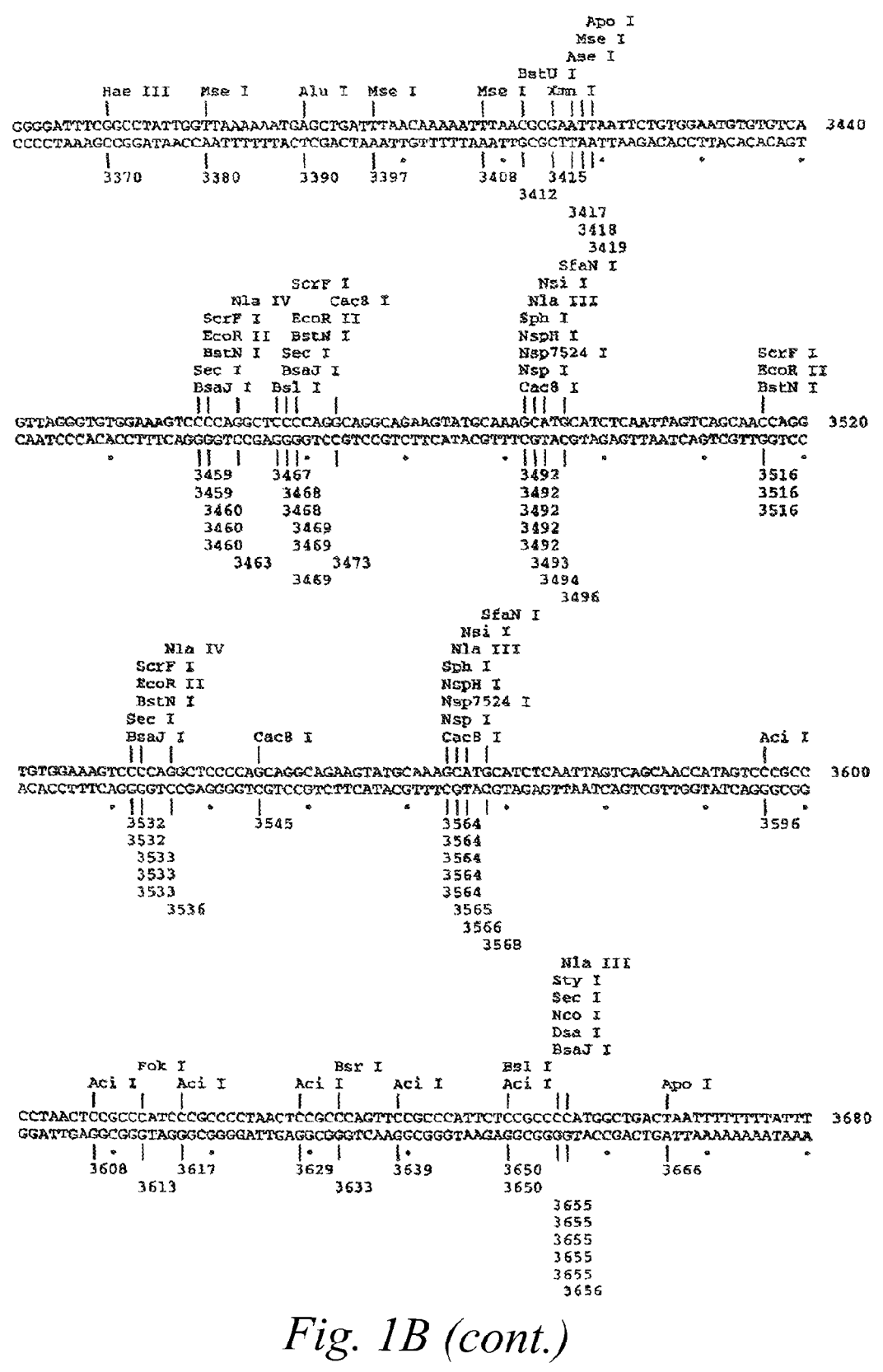
Figure 1B:
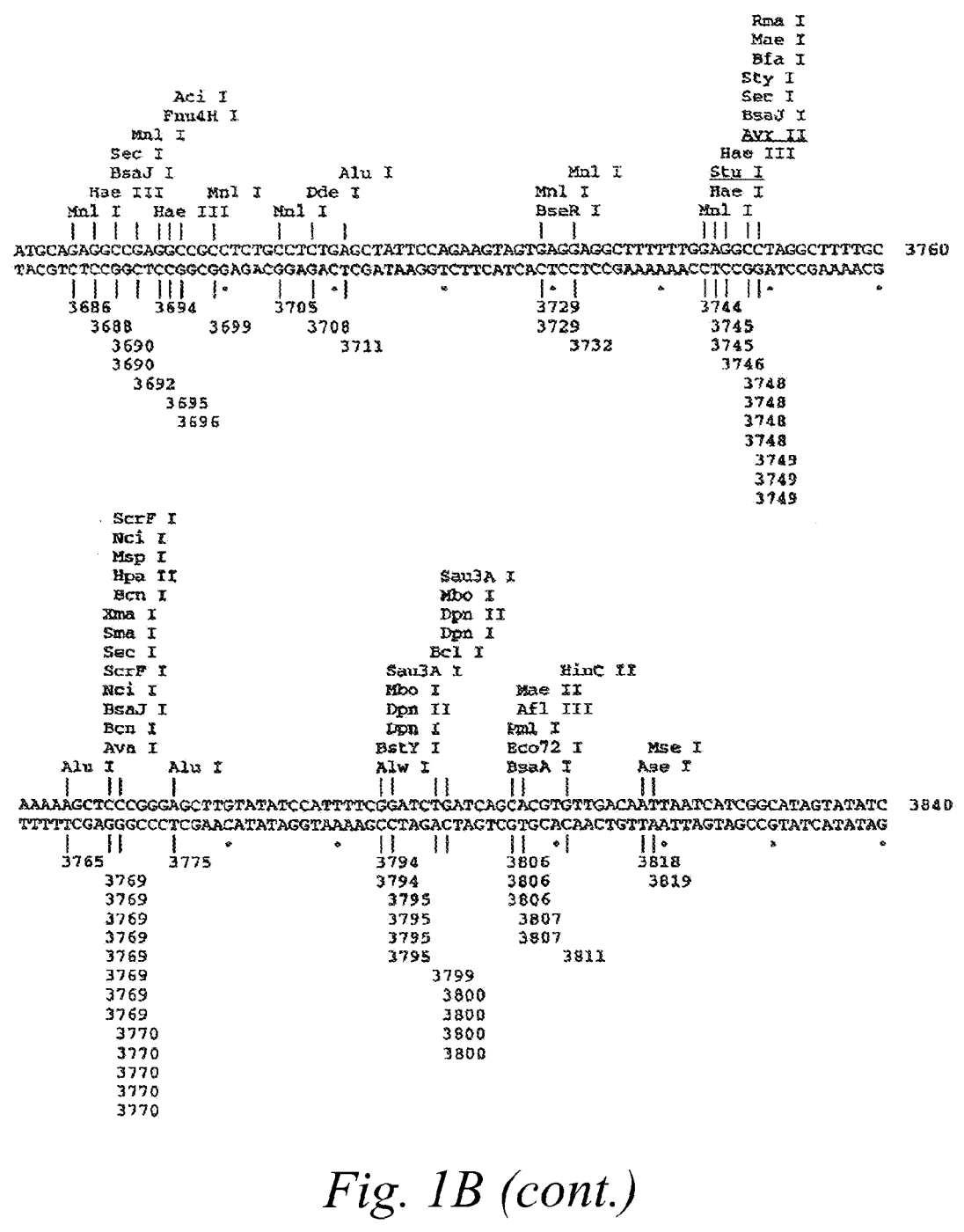
Figure 1B:
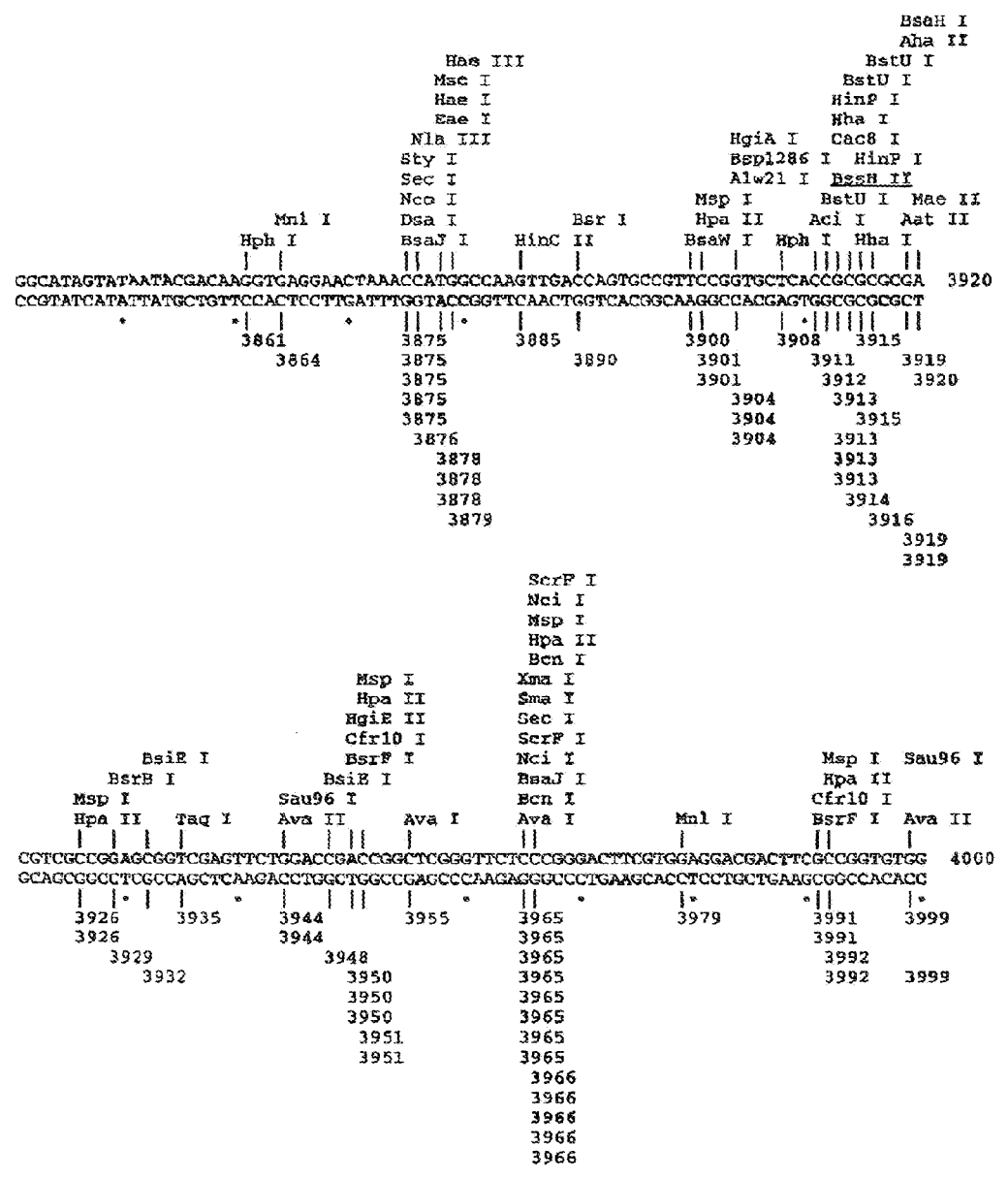
Figure 1B:
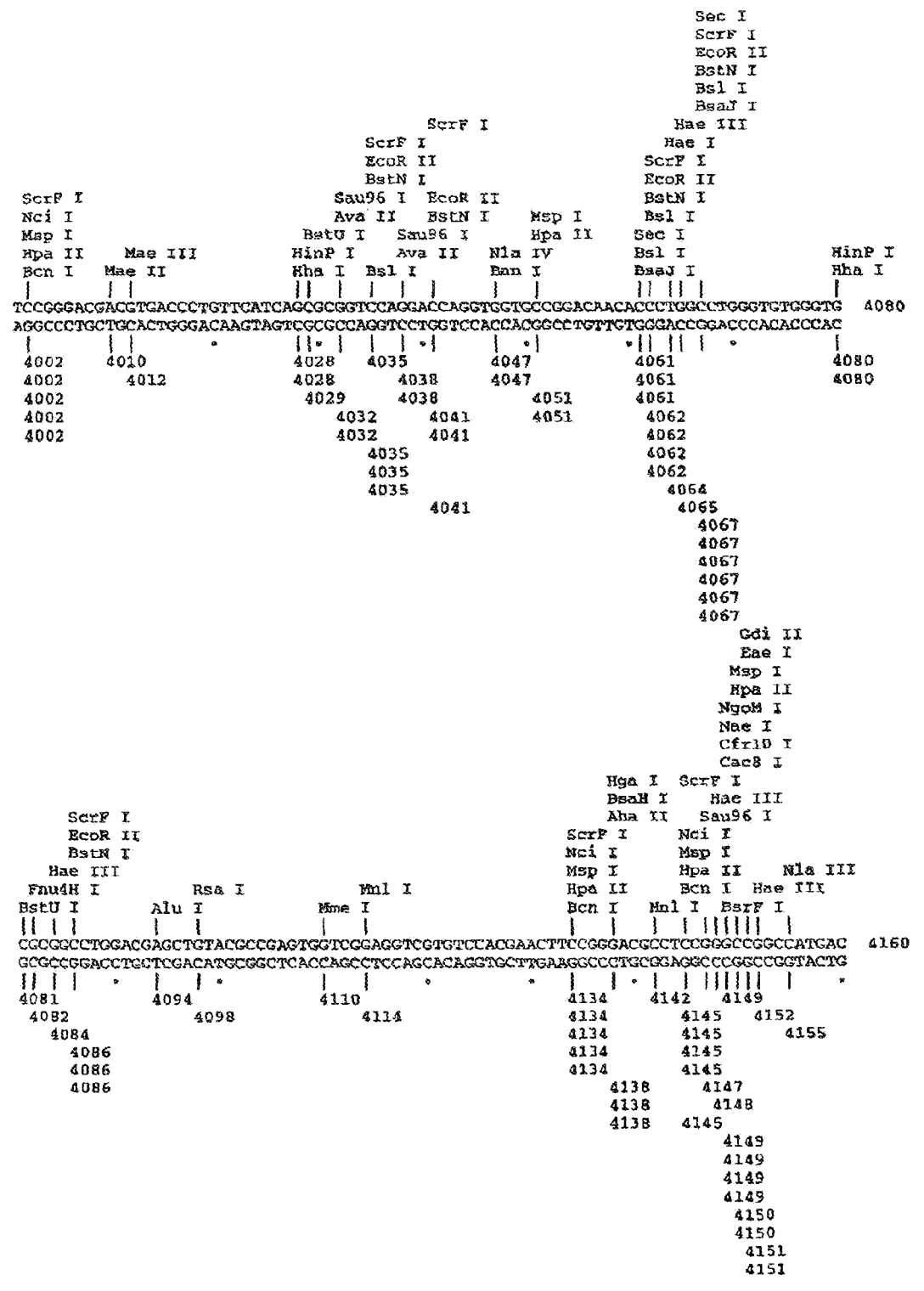
Figure 1B:
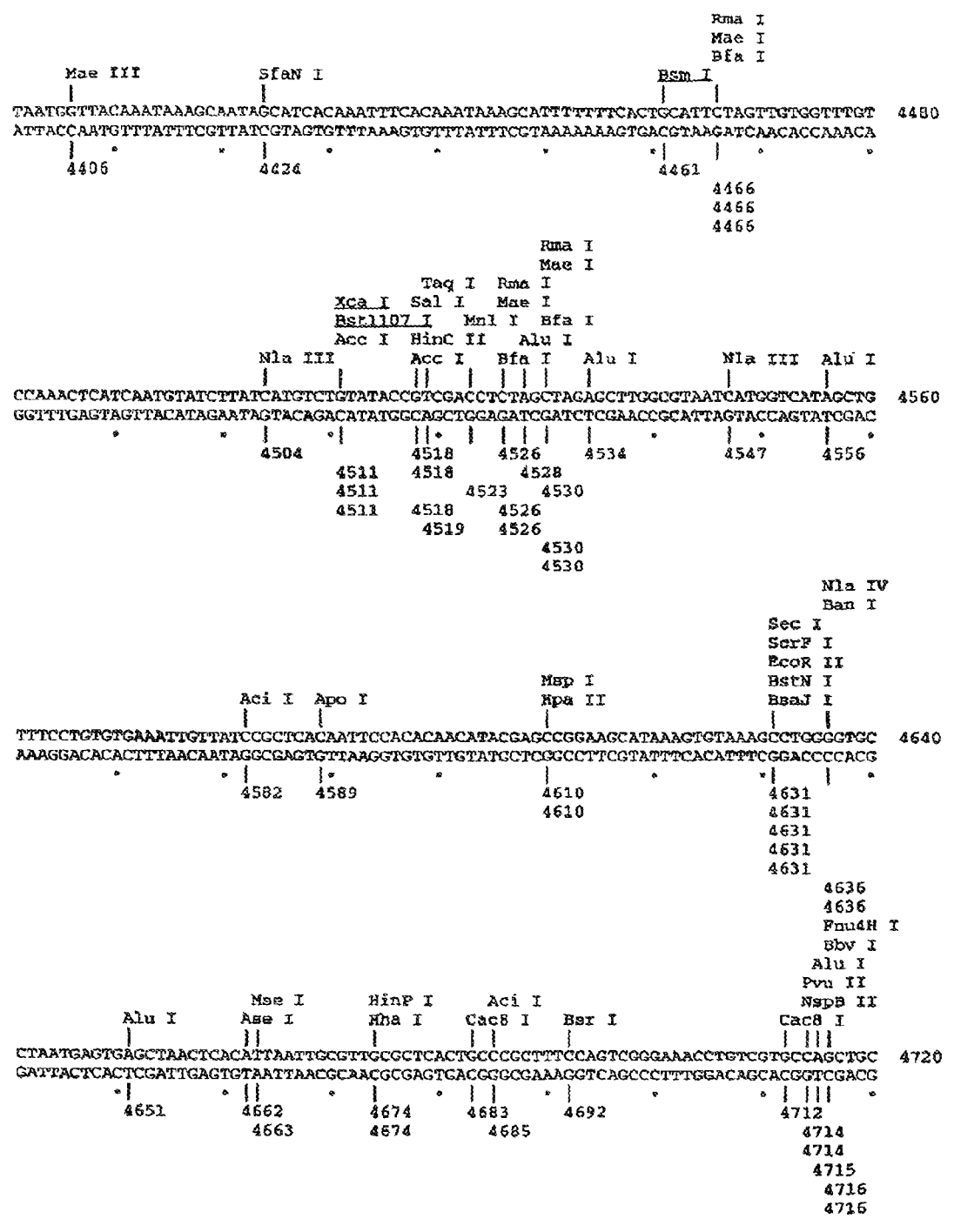
Figure 1B:
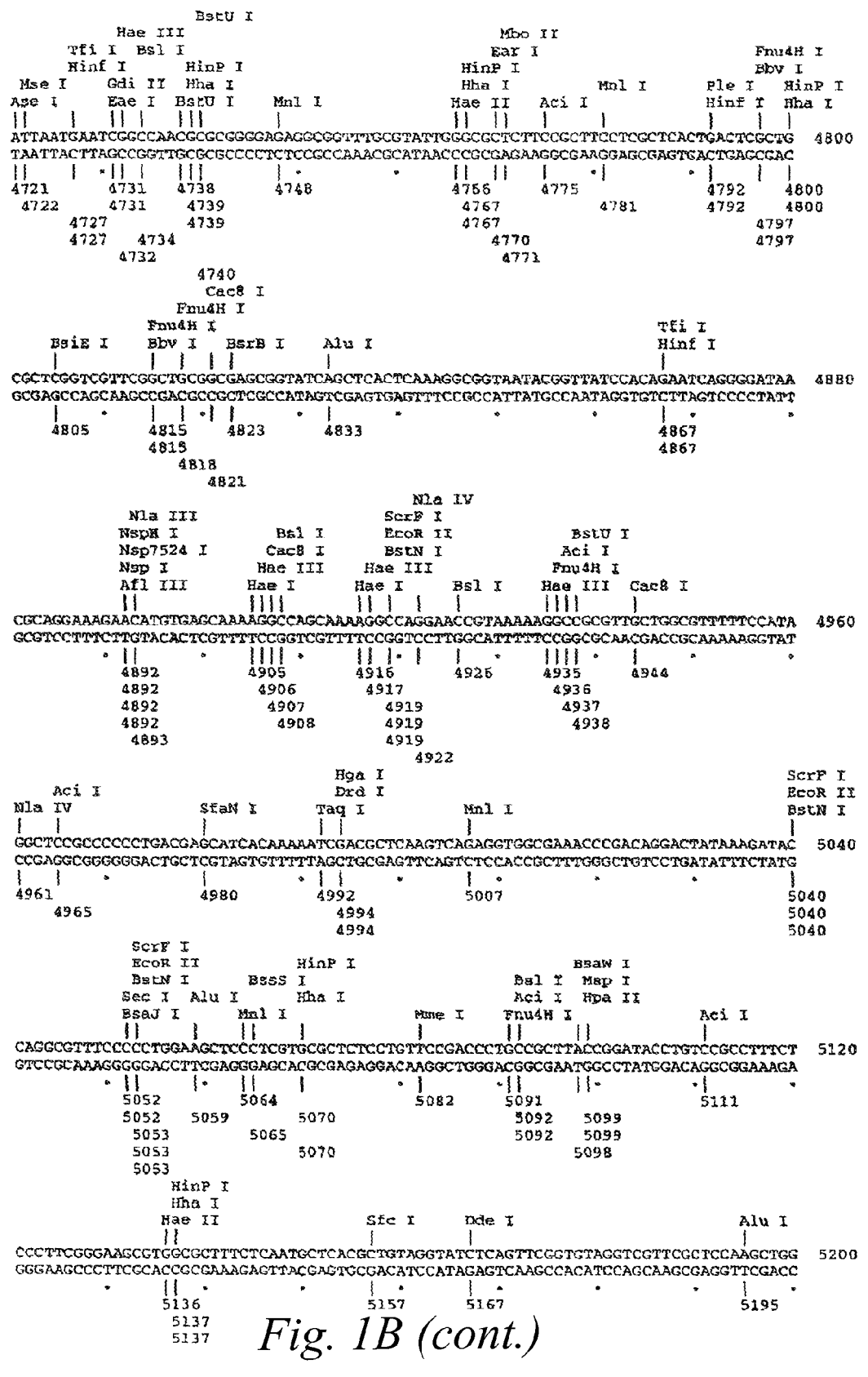
Figure 1B:
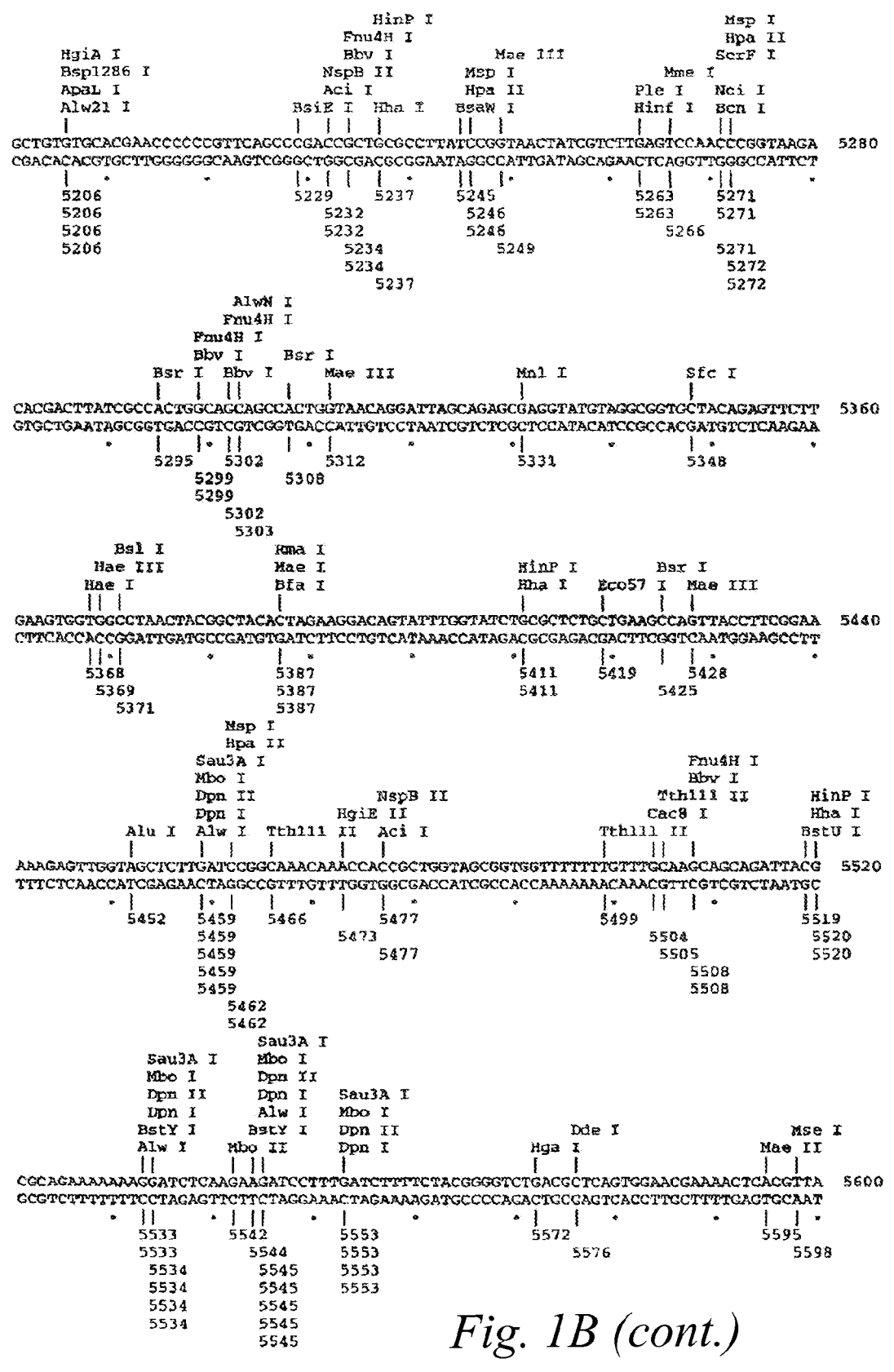
Figure 1B:
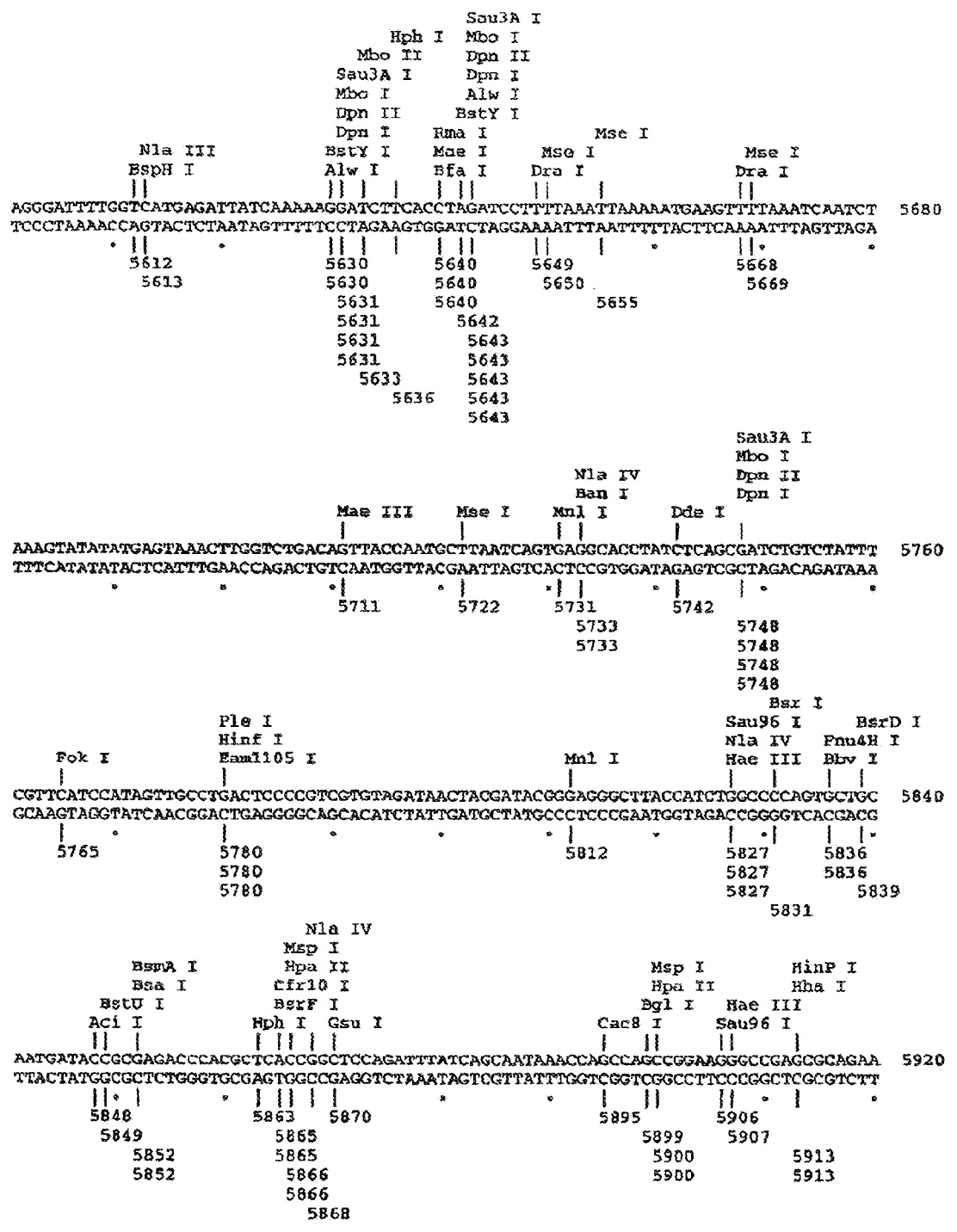
Figure 1B:
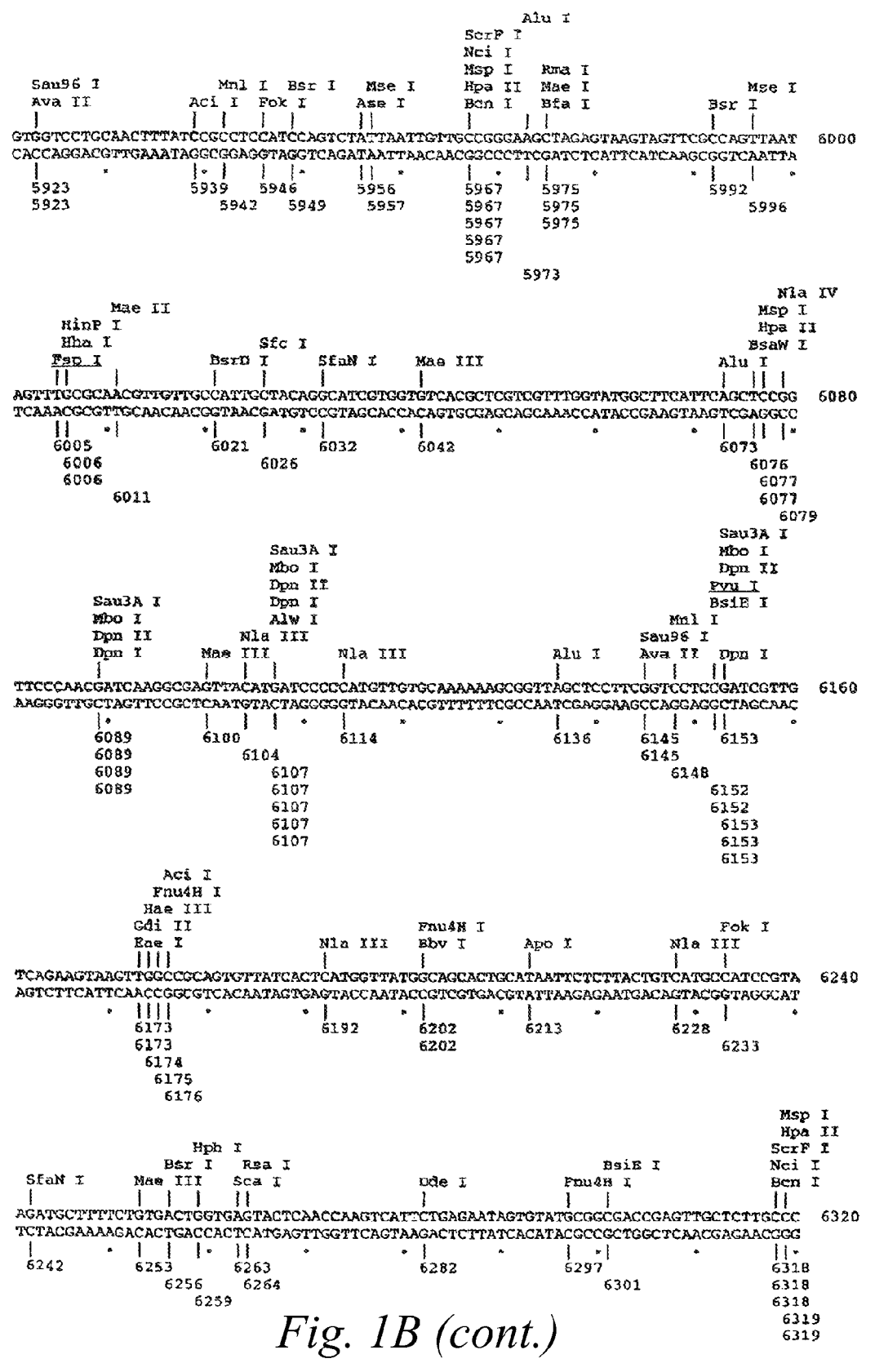
Figure 1B:
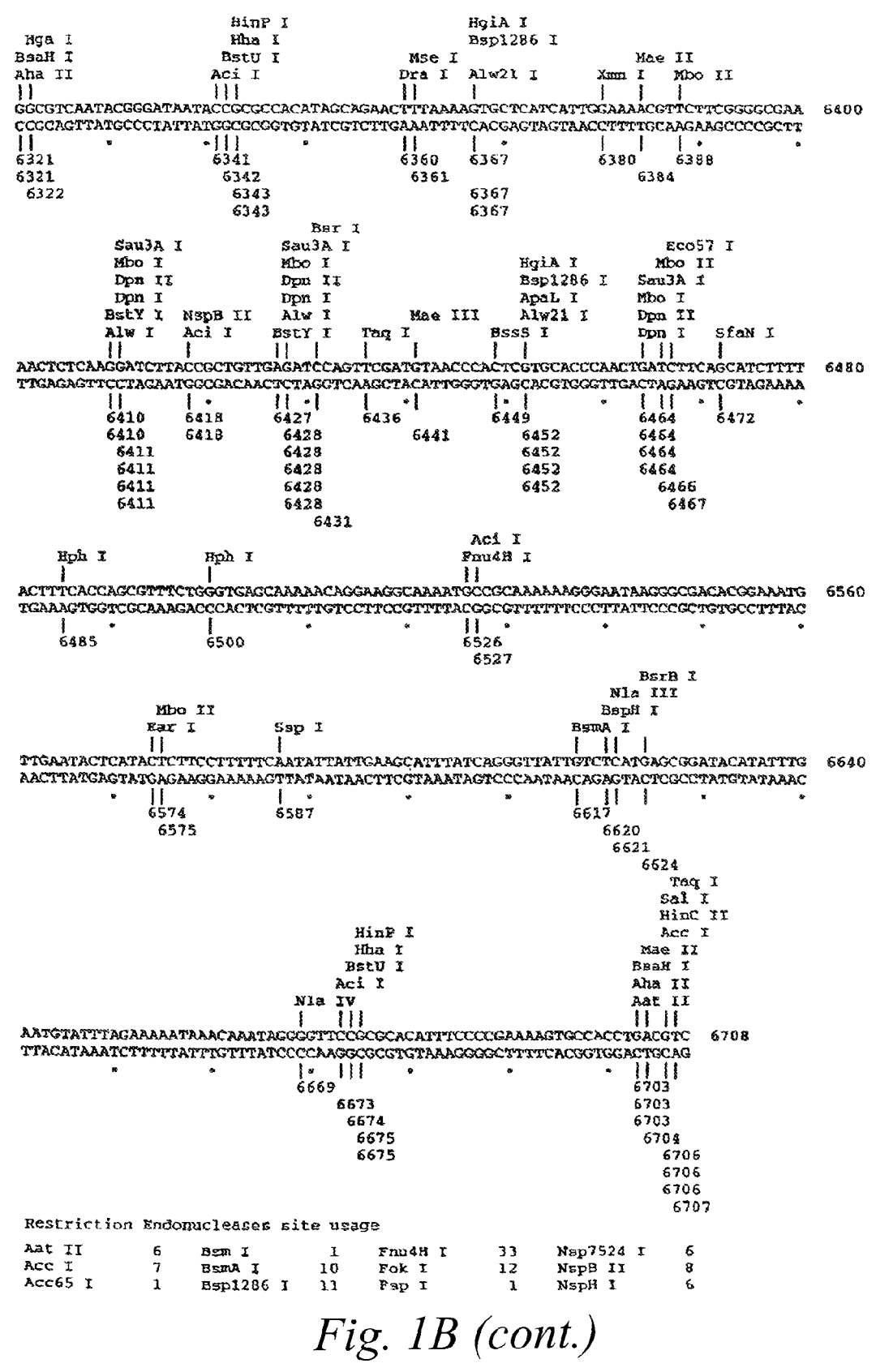
Figure 1C:
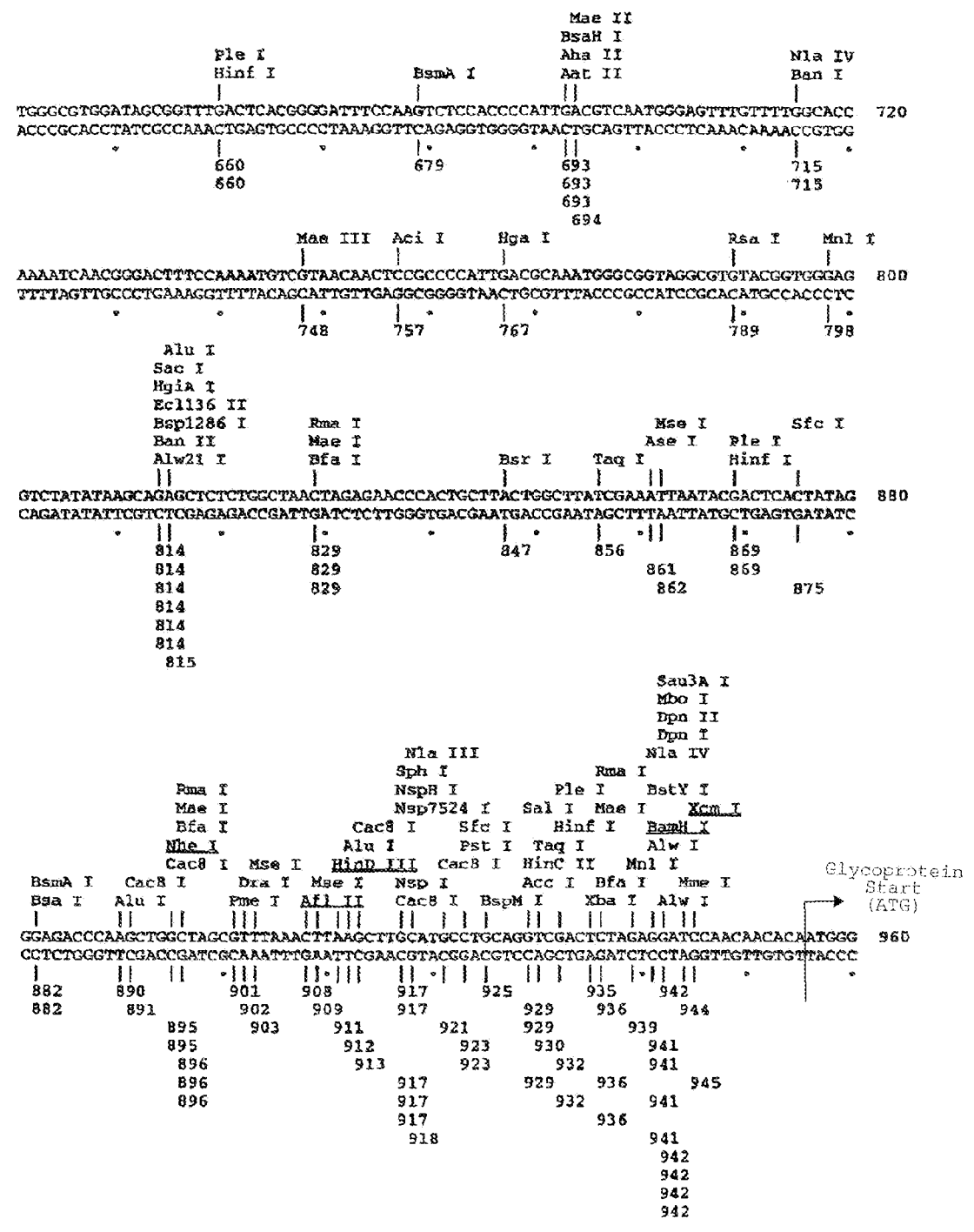
Figure 1C:
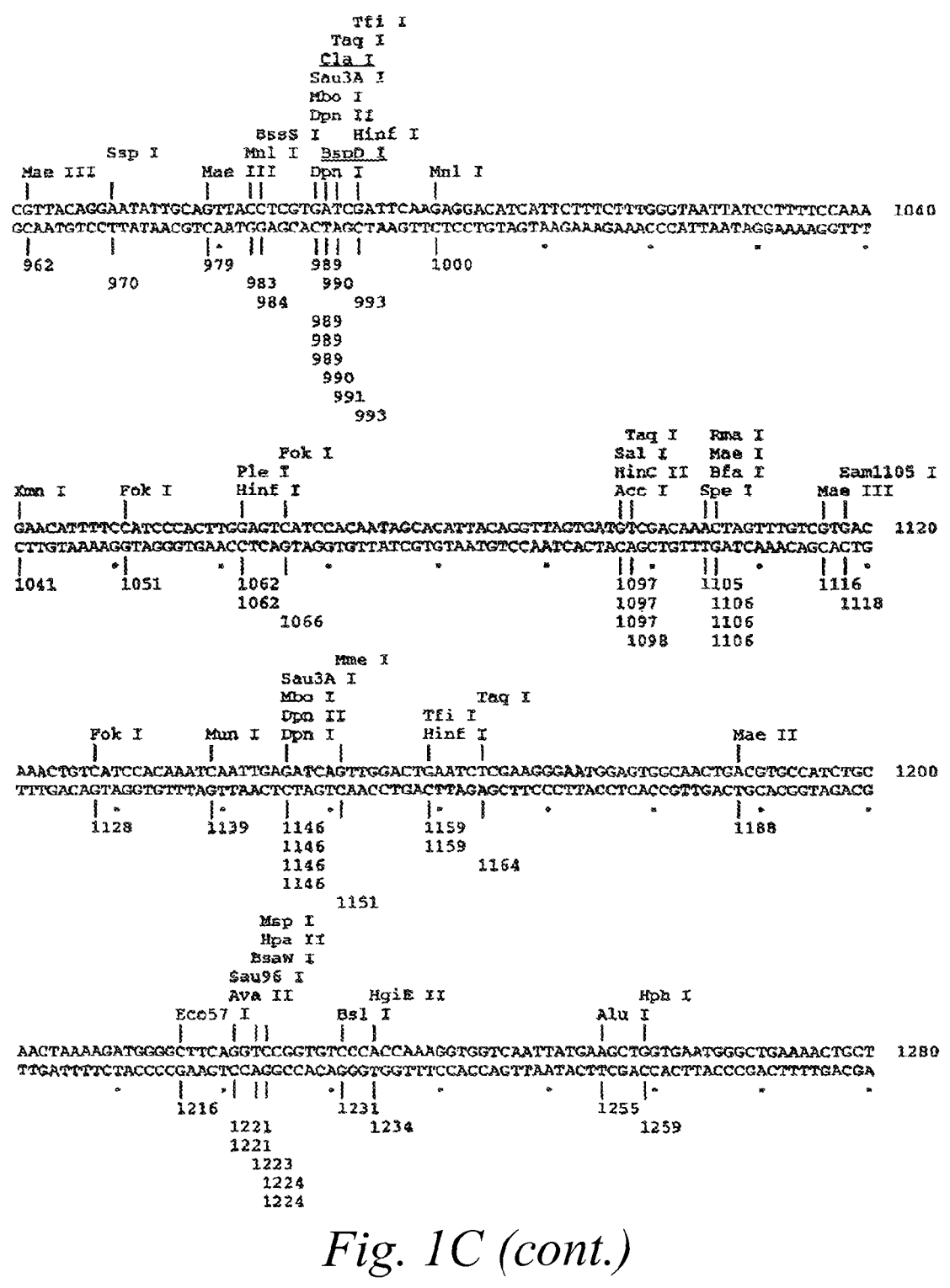
Figure 1C:
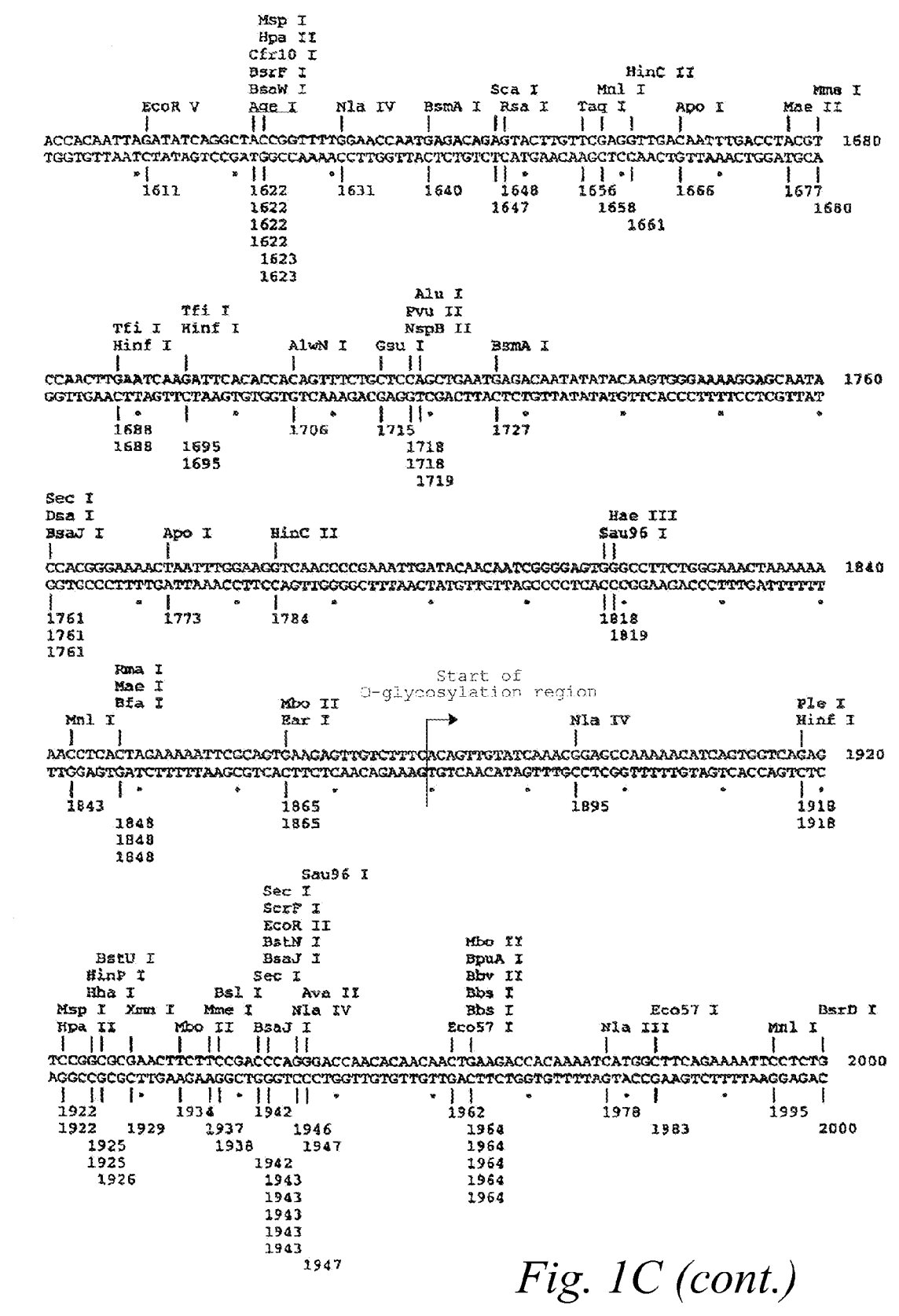
Figure 1C:
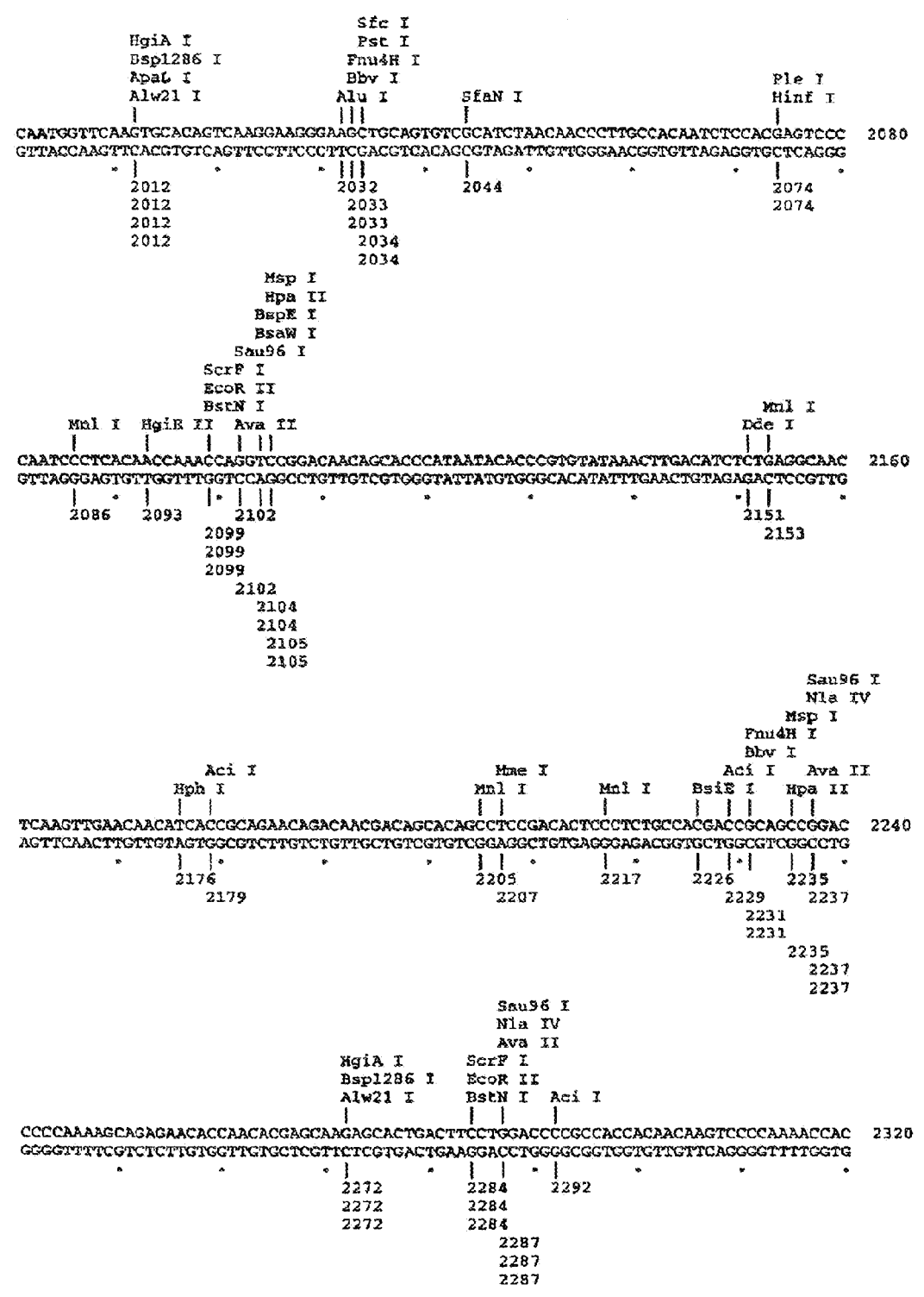
Figure 1C:
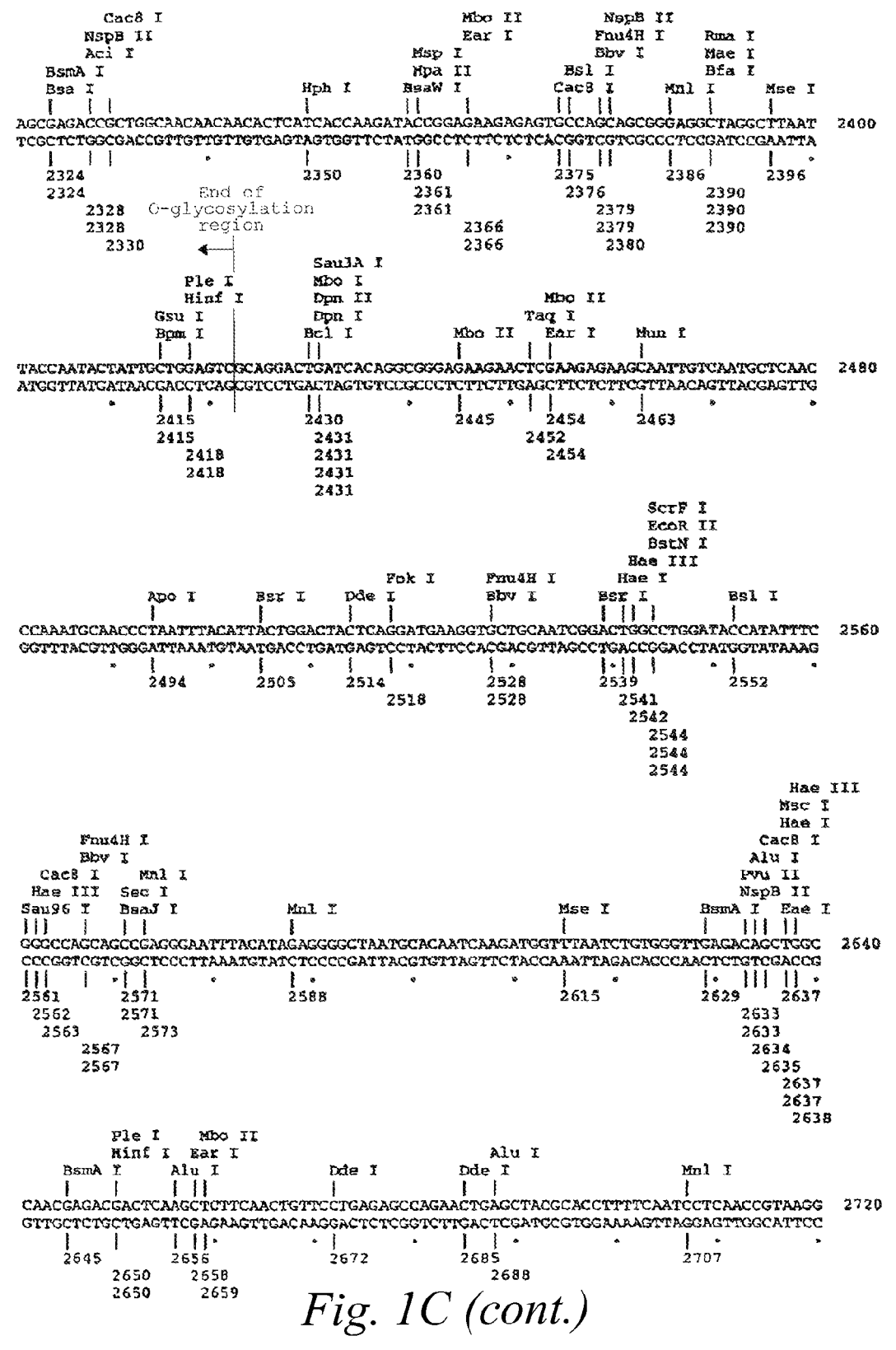

The GP clone in which the mucin region was deleted (Δ309-489) was generated from two PCR clones linked by an XbaI restriction site, which resulted in the replacement of the mucin sequence with two residues (serine-arginine). Mutations in isolated plasmid clones were identified by direct sequencing of mini-prep DNA using dye-terminator cycle sequencing reactions (ABI) analyzed on either an ABI 373 or 377 sequencer. Large-scale preparations for each type of mutated plasmid DNA were made using commercial kits (Promega Corp. or 5 Prime→3 Prime, Inc.). The DNA was quantified by $UV_{260}$ absorbance readings, and then stored at −70° C. until needed. The coding region (BamHI/SalI fragments) from the plasmid pTM1(ΔNcoI)-GP and mutated versions of this DNA were separately ligated into the BamHI/XhoI polylinker sites of the vector pcDNA3 (Invitrogen) to yield pEboGP (FIG. 1C) and pEboGPΔ309-489 (FIG. 1B). These plasmids were then cloned in E. coli, and plasmid DNA was isolated for use in pseudotyping studies.

Retrovirus pseudotyping and virus transduction assays. Pseudotyped retrovirus particles consisting of the MuLV cores and the Ebola GP in their envelopes were produced by transfecting wild-type or mutated plasmid DNA into gpnlslacZ cells as previously described by Sharkey et al. (J. Virol. 75:2653-2659 (2001)). Virus transduction of β-galactosidase activity into NIH 3T3 cells was determined as described by Sharkey et al. (J. Virol. 75:2653-2659 (2001)). All data presented are the average of the results of at least three experiments.

Immunoblot analysis of Ebola virus glycoprotein expression, processing, and incorporation into pseudotyped retroviruses. Medium from transfected φNX cells (Grignani et al., Cancer Res 58:14-19 (1998); Sanchez et al., J Virol 72:6442-6447 (1998); Swift et al., p. 10.17.14-10.17.29. In R. Coico (ed.), Current Protocols in Immunology supp. 31. J. Wiley & Sons (1999)) containing recombinant retroviruses were passed through a 0.45 μm filter and centrifuged through a 30% sucrose cushion at 25,000 RPM in a Beckman 50.2-Ti rotor in a Beckman SS-71 centrifuge. The fluid was aspirated from centrifuge tubes and discarded, and the virus pellet was suspended in 100 μl of RIPA buffer (140 mM NaCl, 10 mM Tris HCl pH 8.0, 5 mM EDTA, 1% Na deoxycholate, 1% Triton X-100, 0.1% SDS). Cells were treated with lysis buffer (50 mM Tris HCl pH 8.0, 5 mM EDTA, 150 mM NaCl, 1% Triton X-100), and the cell lysates were then centrifuged in a microcentrifuge at 16,100×g for ten minutes. The proteins in the cell lysate and the suspended viral pellet were each precipitated with a final concentration of 4% TCA for two minutes. The precipitated proteins were then centrifuged at 16,100×g in a microcentrifuge for ten minutes. The supernatant fluid was aspirated and discarded. The pellet was suspended in an equal volume of 1 M Tris[hydroxymethyl]-aminomethane and vortexed vigorously. Proteins whose glycosylation was analyzed were treated sequentially with PNGase F, which removes N-linked glycosylation, and with both Sialidase A and Endo-O-glycosidase (ProZyme, Inc.), which together remove O-linked glycosylation, following protocols provided by the supplier. The pellet suspension was then mixed with ⅙ the volume of 300 mM Tris pH 6.8, 60% glycerol (w/v), 4% SDS (w/v), 0.0012% bromophenol blue (w/v), 6% 2-mercaptoethanol (v/v) and boiled for 5 minutes.

Equal amounts of proteins as determined by the Bradford assay were separated by SDS-PAGE (8.5% acrylamide), and electrophoretically blotted onto nitrocellulose membranes. Membrane blots were immersed in reaction buffer (20 mM Tris, 137 mM NaCl, 0.1% Tween 20, pH 7.6) containing 1% bovine serum albumin and incubated overnight at 4° C. Blots were incubated in reaction buffer containing a rabbit-anti-Ebola SGP/GP diluted 1:1000 for 1 hour at room temperature, washed 3 times in reaction buffer, and reacted with a Goat anti-rabbit-horseradish peroxidase conjugate (diluted 1:20,000 in reaction buffer) for 30 minutes at room temperature. Membranes were washed as before, then treated with a commercial chemiluminescent substrate solution (Amersham Pharmacia Biotech), according to the protocols provided by the manufacturer. Specific reactivity to GP was visualized by exposing treated blots to X-ray film.

Results

Figure 2:
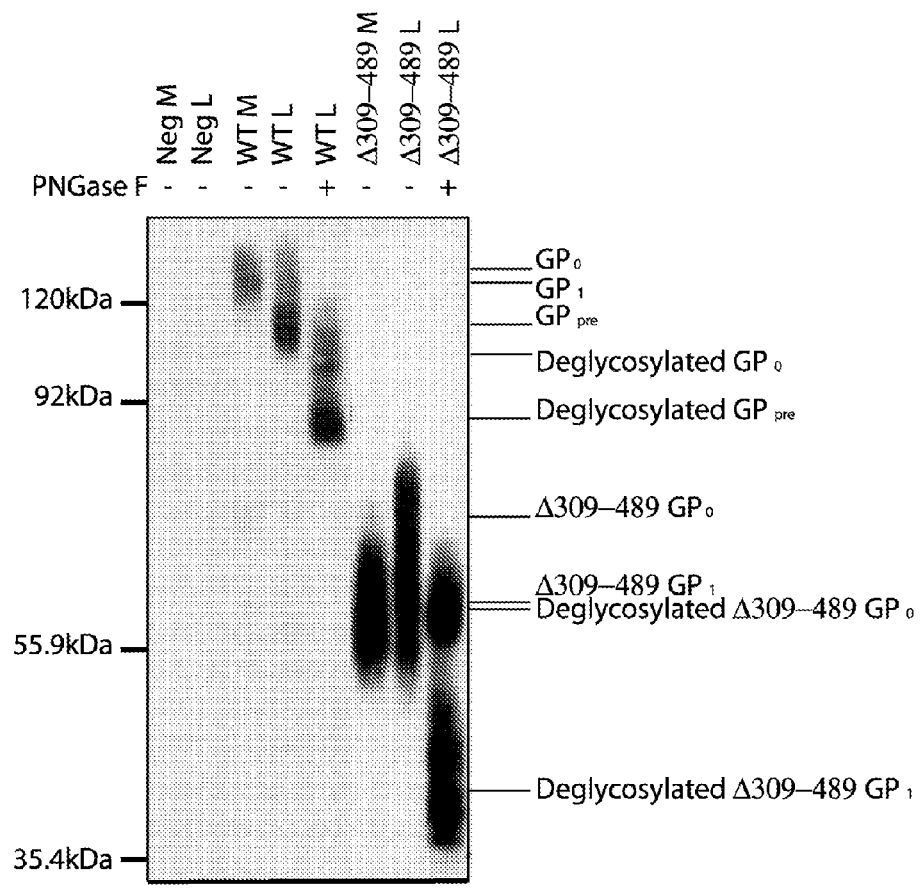
FIG. 2 is a western blot showing the expression and incorporation of the Δ0309-489 Ebola GP into pseudotyped retrovirus.
Figure 3:
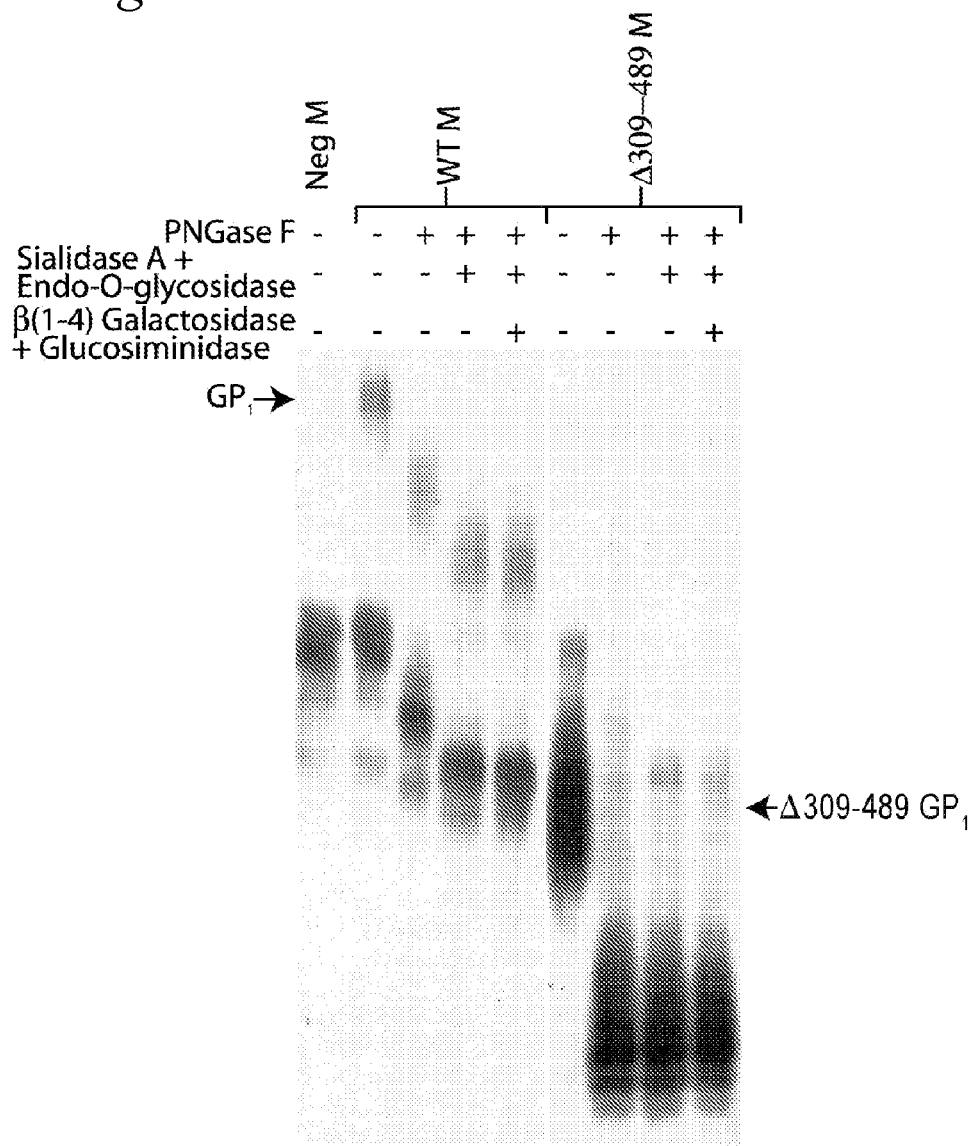
FIG. 3 is a western blot showing the extent of O-glycosylation of the Δ309-489 Ebola GP incorporated into pseudotyped retroviruses.

Pseudotyped retroviruses bearing GPs with altered glycosylation. The role of O-glycosylation of the Ebola virus GP was examined through analysis of the effects of deleting the region of the protein that is O-glycosylated (Jeffers et al., J Virol 2002 December; 76(24): 12463-72). Remarkably, processing and viral incorporation of the Δ309-489 GP was greatly enhanced as shown in FIG. 2. The migration of the mature $GP_1$, $GP_0$ (the glycosylated but uncleaved glycoform), $GP_{pre}$ (the N-glycosylated but not O-glycosylated uncleaved glycoform) and deglycosylated $GP_0$ and $GP_{pre}$ forms of the wild-type GP and of the $GP_1$, $GP_0$ and deglycosylated $GP_1$ and $GP_0$ forms of the Δ309-489 GP is indicated. There was also a corresponding increase of 696±142% in transduction by the Δ309-489 GP pseudotyped viruses as compared to wild type. The absence of an increase in the mobility of the Δ309-489 GP upon sialadase A and endo-O-glycosidase treatment provides confirmation that the region of O-glycosylation of the glycoprotein has been removed (FIG. 3). The migration of the mature $GP_1$ of the wild-type and Δ309-489 GPs is indicated. In this experiment a glycosylated serum protein possessing a mobility intermediate between those of the wild-type and Δ309-489 $GP_1$s was detected. The heterogeneous mobility of the PNGaseF-treated proteins is indicative of incomplete removal of N-glycosylation.

The effect of deleting the O-glycosylation region of GP, (Δ309-489) on expression and transduction were striking. This segment, which is rich in proline, serine, and threonine residues is the most variable among the Ebola GPs. Elimination of this mucin-like region results in enhanced GP processing and incorporation into retroviral particles (FIG. 2) and consequently higher levels of transduction by the pseudotyped retroviruses. It is possible that the wild-type GP is retained in the Golgi apparatus until all of the serines and threonine residues in the mucin region are modified. While not wishing to be bound by theory, it is thought that elimination of this segment may permit more rapid transit through the Golgi apparatus and higher levels of processing to $GP_1$ and $GP_2$ and of cell-surface expression. Increased viral incorporation may also result from a diminution of GP toxicity. It has been reported that the deletion of the O-glycosylation region reduces the cytopathic effects of Ebola virus GP expression (Yang et al., Science, 279:1034-1037 (1998)). It has also been suggested that the expression of high levels of the wild-type Ebola GP might lead to exhaustion of the cellular glycosylation machinery (Volchkov et al., Science, 291:1965-9 (2001)), which is consistent with the present results and present interpretation.

Example II

Expression of Green Fluorescent Protein in Target Cells Transduced with Pseudotyped Retrovirus A plasmid was constructed based on pcDNA3.1 (Invitrogen) expresses the Ebola virus (Zaire strain) glycoprotein with its O-glycosylation region deleted (amino acids 309-489), under control of the cytomegalovirus (CMV) promoter. pcDNA3.1 is similar to pcDNA1 but it also contains zeocin resistance. This plasmid was transfected into human cell lines (gpGFP, Taylor et al., *Mol. Biol. Cell*, 10:2803-2815 (1999)) that have also been transfected with genes encoding the Moloney murine leukemia virus (Mo-MuLV) gag and pol (including pro) genes, the plasmid MFG.S-GFP, and a gene encoding the A. Victoria green fluorescent protein (GFP).

Recombinant pseudotyped retrovirus recovered from the supernatant medium of such cells was incubated with several different cell lines (a murine cell line, NIH3T3; a human cell line, HeLa; and a hamster cell line, BHK) and was shown to be capable of introducing the gene encoding the green fluorescent protein into the target cells. Transduction levels associated with the modified pseudovirus were 4.7 fold higher than with the retroviruses pseudotyped with unmodified (native) Ebola virus glycoprotein. These recombinant modified Ebola glycoprotein-pseudotyped retroviruses have substantially improved titers that make in vivo gene transfer and gene therapy experiments with such viruses feasible for the first time.

Example III

Feline Immunodeficiency Virus Pseudotyped with Ebola Glycoprotein Lacking O-Glycosylation Region Feline immunodeficiency virus (FIV)-based vectors, which are a non-primate lentivirus vectors, were pseudotyped using envelope glycoproteins (GPs) from the filoviruses Marburg and Ebola virus (Sinn et al., J Virol 2003 May 15; 77(10):5902-10). We observed that primary cultures of well-differentiated human airway epithelia were transduced when filovirus GP pseudotyped FIV was applied to the apical surface. Furthermore, by deleting a heavily O-glycosylated extracellular region of the Ebola GP, we improved the titer of concentrated vector several fold.

Vector production. The second-generation FIV vector system utilized in this study was reported previously (Johnston et al., *J. Virol.* 73:4991-5000 (1999) and Wang et al., *J. Clin. Inv.* 104:R55-62 (1999)). The FIV vector construct expressed the β-galactosidase cDNA directed by the CMV promoter. EBOΔO (pEZGP 309-489) has been previously described (Jeffers et al., *J. Virol.*, 76:12463-12472 (2002); Example I). Pseudotyped FIV vector particles were generated by transient transfection of plasmid DNA into 293T cells as described previously (Johnston et al., *J. Virol.* 73:4991-5000 (1999)). FIV vector preparations were titered on HT1080 cells at limiting dilutions and these titers were used to calculate the multiplicities of infection (MOIs). In addition, we found that the filoviral glycoprotein conferred enough stability to the lentiviral vector to withstand centrifuge concentration of greater 1000-fold (data not shown); however, we typically concentrated vector 250-fold by centrifugation for in vitro experiments.

Deletion of the O-glycosylated region from the extracellular domain of filoviral glycoproteins. An initial strategy for enhancing filoviral pseudotyped FIV-vector titer was to delete an expansive region from the extracellular domain thought to be heavily O-glycosylated. By deleting this region, the efficiency of envelope protein synthesis and transport to the cell surface is enhanced (Example I). This region may be functionally less important than the flanking regions of the protein simply because of little sequence conservation in this region among all filoviral isolates. The deletion of amino acids 309-489 from the Ebola glycoprotein (EBOΔO) resulted in a marked 74-fold increase in titer over the average titer obtained with the wild-type Ebola glycoprotein.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A pseudotyped retrovirus comprising a recombinant RNA associated with a retroviral core surrounded by a lipid bilayer having disposed therein modified Ebola glycoprotein, wherein the modified glycoprotein contains a deletion of amino acids 309-489 in the O-glycosylation region of a wild-type Ebola glycoprotein encoded by SEQ ID NO:1, wherein the recombinant RNA comprises (i) a nucleotide sequence defining a selected biomolecule intended for delivery to a target cell, and (ii) retroviral control elements for packaging, reverse transcription and integration of the retrovirus into a target cell, and wherein the pseudotyped retrovirus has a transduction efficiency into a target cell of at least 2-fold higher than a retrovirus pseudotyped with the wild-type Ebola glycoprotein.

2. The pseudotyped retrovirus of claim 1, wherein the retroviral core and control elements are from Moloney murine leukemia virus (Mo-MuLV).

3. The pseudotyped retrovirus of claim 1, wherein the retroviral core and control elements are from a lentivirus.

4. The pseudotyped retrovirus of claim 3, wherein the lentivirus is feline immunodeficiency virus (FIV), human immunodeficiency virus (HIV), simian immunodeficiency virus (SIV) or equine infectious anemia virus (EIAV).

5. The pseudotyped retrovirus of claim 1, wherein the selected biomolecule is a protein.

6. The pseudotyped retrovirus of claim 1, wherein the selected biomolecule is a bioactive RNA.

7. A recombinant retrovirus pseudotyped with a modified Ebola glycoprotein lacking amino acids 309-489 in the O-glycosylation region of a wild-type Ebola glycoprotein encoded by SEQ ID NO:1, wherein said recombinant retrovirus has a transduction efficiency into a target cell of at least 2-fold higher than a retrovirus pseudotyped with the wild-type glycoprotein.

\* \* \* \* \*

```
                         SEQUENCE LISTING

<160> NUMBER OF SEQ ID NOS: 2

<210> SEQ ID NO 1
<211> LENGTH: 2400
<212> TYPE: DNA
<213> ORGANISM: artificial
<220> FEATURE:
<223> OTHER INFORMATION: plasmid pEboGP

<400> SEQUENCE: 1
tgggcgtgga tagcggtttg actcacgggg atttccaagt ctccacccca ttgacgtcaa      60
tgggagtttg ttttggcacc aaaatcaacg ggactttcca aaatgtcgta acaactccgc     120
cccattgacg caaatgggcg gtaggcgtgt acggtgggag gtctatataa gcagagctct     180
ctggctaact agagaaccca ctgcttactg gcttatcgaa attaatacga ctcactatag     240
```

-continued

| | |
|---|---|
| ggagacccaa gctggctagc gtttaaactt aagcttgcat gcctgcaggt cgactctaga | 300 |
| ggatccaaca acacaatggg cgttacagga atattgcagt tacctcgtga tcgattcaag | 360 |
| aggacatcat tctttctttg ggtaattatc cttttccaaa gaacattttc catcccactt | 420 |
| ggagtcatcc acaatagcac attacaggtt agtgatgtcg acaaactagt ttgtcgtgac | 480 |
| aaactgtcat ccacaaatca attgagatca gttggactga atctcgaagg gaatggagtg | 540 |
| gcaactgacg tgccatctgc aactaaaaga tggggcttca ggtccggtgt cccaccaaag | 600 |
| gtggtcaatt atgaagctgg tgaatgggct gaaaactgct acaatcttga atcaaaaaa | 660 |
| cctgacggga gtgagtgtct accagcagcg ccagacggga ttcggggctt cccccggtgc | 720 |
| cggtatgtgc acaaagtatc aggaacggga ccgtgtgccg gagactttgc cttccataaa | 780 |
| gagggtgctt tcttcctgta tgatcgactt gcttccacag ttatctaccg aggaacgact | 840 |
| ttcgctgaag gtgtcgttgc atttctgata ctgccccaag ctaagaagga cttcttcagc | 900 |
| tcacacccct tgagagagcc ggtcaatgca acggaggacc cgtctagtgg ctactattct | 960 |
| accacaatta gatatcaggc taccggtttt ggaaccaatg agacagagta cttgttcgag | 1020 |
| gttgacaatt tgacctacgt ccaacttgaa tcaagattca caccacagtt tctgctccag | 1080 |
| ctgaatgaga caatatatac aagtgggaaa aggagcaata ccacgggaaa actaatttgg | 1140 |
| aaggtcaacc ccgaaattga tacaacaatc ggggagtggg ccttctggga aactaaaaaa | 1200 |
| aacctcacta gaaaaattcg cagtgaagag ttgtctttca cagttgtatc aaacggagcc | 1260 |
| aaaaacatca gtggtcagag tccggcgcga acttcttccg acccagggac caacacaaca | 1320 |
| actgaagacc acaaaatcat ggcttcagaa aattcctctg caatggttca agtgcacagt | 1380 |
| caaggaaggg aagctgcagt gtcgcatcta acaaccttg ccacaatctc cacgagtccc | 1440 |
| caatccctca caaccaaacc aggtccggac aacagcaccc ataatacacc cgtgtataaa | 1500 |
| cttgacatct ctgaggcaac tcaagttgaa caacatcacc gcagaacaga caacgacagc | 1560 |
| acagcctccg acactccctc tgccacgacc gcagccggac cccaaaagc agagaacacc | 1620 |
| aacacgagca agagcactga cttcctggac cccgccacca acaagtcc caaaaccac | 1680 |
| agcgagaccg ctggcaacaa caacactcat caccaagata ccggagaaga gagtgccagc | 1740 |
| agcgggaggc taggcttaat taccaatact attgctggag tcgcaggact gatcacaggc | 1800 |
| gggagaagaa ctcgaagaga agcaattgtc aatgctcaac ccaaatgcaa ccctaattta | 1860 |
| cattactgga ctactcagga tgaaggtgct gcaatcggac tggcctggat accatatttc | 1920 |
| gggccagcag ccgagggaat ttacatagag ggctaatgc acaatcaaga tggtttaatc | 1980 |
| tgtgggttga cagctggc caacgagacg actcaagctc ttcaactgtt cctgagagcc | 2040 |
| agaactgagc tacgcacctt ttcaatcctc aaccgtaagg caattgattt cttgctgcag | 2100 |
| cgatggggcg gcacatgcca cattctggga ccggactgct gtatcgaacc acatgattgg | 2160 |
| accaagaaca taacagacaa aattgatcag attattcatg attttgttga taaaacccctt | 2220 |
| ccggaccagg gggacaatga caattggtgg acaggatgga gacaatggat accggcaggt | 2280 |
| attggagtta caggcgttat aattgcagtt atcgctttat tctgtatatg caaatttgtc | 2340 |
| ttttagtttt tcttcagatt gcttcatgga aaagctcagc ctcaaatcaa tgaaaccaga | 2400 |

<210> SEQ ID NO 2
<211> LENGTH: 6708
<212> TYPE: DNA
<213> ORGANISM: artificial
<220> FEATURE:
<223> OTHER INFORMATION: plasmid pEboGPdelta309-489

```
<400> SEQUENCE: 2
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttgcat gcctgcaggt cgactctaga ggatccaaca acacaatggg     960
cgttacagga atattgcagt tacctcgtga tcgattcaag aggacatcat tctttctttg    1020
ggtaattatc cttttccaaa gaacattttc catcccactt ggagtcatcc acaatagcac    1080
attacaggtt agtgatgtcg acaaactagt ttgtcgtgac aaactgtcat ccacaaatca    1140
attgagatca gttggactga atctcgaagg gaatggagtg gcaactgacg tgccatctgc    1200
aactaaaaga tggggcttca ggtccggtgt cccaccaaag gtggtcaatt atgaagctgg    1260
tgaatgggct gaaaactgct acaatcttga aatcaaaaaa cctgacggga gtgagtgtct    1320
accagcagcg ccagacggga ttcggggctt ccccggtgc cggtatgtgc acaaagtatc    1380
aggaacggga ccgtgtgccg gagactttgc cttccataaa gagggtgctt tcttcctgta    1440
tgatcgactt gcttccacag ttatctaccg aggaacgact ttcgctgaag gtgtcgttgc    1500
atttctgata ctgccccaag ctaagaagga cttcttcagc tcacacccct tgagagagcc    1560
ggtcaatgca acggaggacc cgtctagtgg ctactattct accacaatta gatatcaggc    1620
taccggtttt ggaaccaatg agacagagta cttgttcgag gttgacaatt tgacctacgt    1680
ccaacttgaa tcaagattca caccacagtt tctgctccag ctgaatgaga caatatatac    1740
aagtgggaaa aggagcaata ccacgggaaa actaatttgg aaggtcaacc ccgaaattga    1800
tacaacaatc ggggagtggg ccttctggga aactaaaaaa aacctcacta gaaaaattcg    1860
cagtgaagag ttgtctttct ctagagcagg actgatcaca gcgggagaa gaactcgaag    1920 agaagcaatt gtcaatgctc aacccaaatg caaccctaat ttacattact ggactactca    1980
ggatgaaggt gctgcaatcg gactggcctg gataccatat ttcgggccag cagccgaggg    2040
aatttacata gaggggctaa tgcacaatca agatggttta atctgtgggt tgagacagct    2100
ggccaacgag acgactcaag ctcttcaact gttcctgaga gccacaactg agctacgcac    2160
cttttcaatc ctcaaccgta aggcaattga tttcttgctg cagcgatggg gcggcacatg    2220
ccacattctg ggaccggact gctgtatcga accacatgat tggaccaaga acataacaga    2280
caaaattgat cagattattc atgattttgt tgataaaacc cttccggacc aggggacaa     2340
```

```
tgacaattgg tggacaggat ggagacaatg gataccggca ggtattggag ttacaggcgt    2400
tataattgca gttatcgctt tattctgtat atgcaaattt gtcttttagt ttttcttcag    2460
attgcttcat ggaaaagctc agcctcaaat caatgaaacc aggatttaat tatatggatt    2520
acttgaatct aagattactt gacaaatgat aatataatac actggagctt taaacatagc    2580
caatgtgatt ctaactcctt taaactcaca gttaatcata aacaaggttt gaggtaccga    2640
gctcgaattc tgcagatatc cagcacagtg gcggccgctc gagtctagag ggcccgttta    2700
aacccgctga tcagcctcga ctgtgccttc tagttgccag ccatctgttg tttgcccctc    2760
ccccgtgcct tccttgaccc tggaaggtgc cactcccact gtcctttcct aataaaatga    2820
ggaaattgca tcgcattgtc tgagtaggtg tcattctatt ctggggggtg gggtggggca    2880
ggacagcaag ggggaggatt gggaagacaa tagcaggcat gctggggatg cggtgggctc    2940
tatggcttct gaggcggaaa gaaccagctg gggctctagg gggtatcccc acgcgccctg    3000
tagcggcgca ttaagcgcgg cgggtgtggt ggttacgcgc agcgtgaccg ctacacttgc    3060
cagcgcccta gcgcccgctc ctttcgcttt cttcccttcc tttctcgcca cgttcgccgg    3120
ctttccccgt caagctctaa atcggggcat ccctttaggg ttccgattta gtgctttacg    3180
gcacctcgac cccaaaaaac ttgattaggg tgatggttca cgtagtgggc catcgccctg    3240
atagacggtt tttcgccctt tgacgttgga gtccacgttc tttaatagtg gactcttgtt    3300
ccaaactgga acaacactca accctatctc ggtctattct tttgatttat aagggatttt    3360
ggggatttcg gcctattggt taaaaaatga gctgatttaa caaaaattta acgcgaatta    3420
attctgtgga atgtgtgtca gttagggtgt ggaaagtccc caggctcccc aggcaggcag    3480
aagtatgcaa agcatgcatc tcaattagtc agcaaccagg tgtggaaagt ccccaggctc    3540
cccagcaggc agaagtatgc aaagcatgca tctcaattag tcagcaacca tagtcccgcc    3600
cctaactccg cccatcccgc cctaactccg cccagttccg cccattctcc gccccatgg    3660 ctgactaatt ttttttattt atgcagaggc cgaggccgcc tctgcctctg agctattcca    3720
gaagtagtga ggaggctttt ttggaggcct aggcttttgc aaaaagctcc cgggagcttg    3780
tatatccatt ttcggatctg atcagcacgt gttgacaatt aatcatcggc atagtatatc    3840
ggcatagtat aatacgacaa ggtgaggaac taaaccatgg ccaagttgac cagtgccgtt    3900
ccggtgctca ccgcgcgcga cgtcgccgga gcggtcgagt tctggaccga ccggctcggg    3960
ttctcccggg acttcgtgga ggacgacttc gccggtgtgg tccgggacga cgtgaccctg    4020
ttcatcagcg cggtccagga ccaggtggtg ccggacaaca ccctggcctg ggtgtgggtg    4080
cgcggcctgg acgagctgta cgccgagtgg tcggaggtcg tgtccacgaa cttccgggac    4140
gcctccgggc cggccatgac cgagatcggc gagcagccgt ggggcgggga gttcgccctg    4200
cgcgacccgg ccggcaactg cgtgcacttc gtggccgagg agcaggactg acacgtgcta    4260
cgagatttcg attccaccgc cgccttctat gaaaggttgg gcttcggaat cgttttccgg    4320
gacgccggct ggatgatcct ccagcgcggg gatctcatgc tggagttctt cgcccacccc    4380
aacttgttta ttgcagctta taatggttac aaataaagca atagcatcac aaatttcaca    4440
aataaagcat ttttttcact gcattctagt tgtggtttgt ccaaactcat caatgtatct    4500
tatcatgtct gtataccgtc gacctctagc tagagcttgg cgtaatcatg gtcatagctg    4560
tttcctgtgt gaaattgtta tccgctcaca attccacaca acatacgagc cggaagcata    4620
aagtgtaaag cctggggtgc ctaatgagtg agctaactca cattaattgc gttgcgctca    4680
ctgcccgctt tccagtcggg aaacctgtcg tgccagctgc attaatgaat cggccaacgc    4740
```

-continued

```
gcggggagag gcggtttgcg tattgggcgc tcttccgctt cctcgctcac tgactcgctg    4800
cgctcggtcg ttcggctgcg gcgagcggta tcagctcact caaaggcggt aatacggtta    4860
tccacagaat caggggataa cgcaggaaag aacatgtgag caaaaggcca gcaaaaggcc    4920
aggaaccgta aaaaggccgc gttgctggcg ttttt ccata ggctccgccc ccctgacgag    4980
catcacaaaa atcgacgctc aagtcagagg tggcgaaacc cgacaggact ataaagatac    5040
caggcgtttc ccc ctggaag ctccctcgtg cgctctcctg ttccgaccct gccgcttacc    5100
ggatacctgt ccgcctttct cccttcggga agcgtggcgc tttctcaatg ctcacgctgt    5160
aggtatctca gttcggtgta ggtcgttcgc tccaagctgg gctgtgtgca cgaaccccc    5220 gttcagcccg accgctgcgc cttatccggt aactatcgtc ttgagtccaa cccggtaaga    5280
cacgacttat cgccactggc agcagccact ggtaacagga ttagcagagc gaggtatgta    5340
ggcggtgcta cagagttctt gaagtggtgg cctaactacg gctacactag aaggacagta    5400
tttggtatct gcgctctgct gaagccagtt accttcggaa aaagagttgg tagctcttga    5460
tccggcaaac aaaccaccgc tggtagcggt ggtttttttg tttgcaagca gcagattacg    5520
cgcagaaaaa aaggatctca agaagatcct ttgatctttt ctacggggtc tgacgctcag    5580
tggaacgaaa actcacgtta agggattttg gtcatgagat tatcaaaaag gatcttcacc    5640
tagatccttt taaattaaaa atgaagtttt aaatcaatct aaagtatata tgagtaaact    5700
tggtctgaca gttaccaatg cttaatcagt gaggcaccta tctcagcgat ctgtctattt    5760
cgttcatcca tagttgcctg actccccgtc gtgtagataa ctacgatacg ggagggctta    5820
ccatctggcc ccagtgctgc aatgataccg cgagacccac gctcaccggc tccagattta    5880
tcagcaataa accagccagc cggaagggcc gagcgcagaa gtggtcctgc aactttatcc    5940
gcctccatcc agtctattaa ttgttgccgg gaagctagag taagtagttc gccagttaat    6000
agtttgcgca acgttgttgc cattgctaca ggcatcgtgg tgtcacgctc gtcgtttggt    6060
atggcttcat tcagctccgg ttcccaacga tcaaggcgag ttacatgatc ccccatgttg    6120
tgcaaaaaag cggttagctc cttcggtcct ccgatcgttg tcagaagtaa gttggccgca    6180
gtgttatcac tcatggttat ggcagcactg cataattctc ttactgtcat gccatccgta    6240
agatgctttt ctgtgactgg tgagtactca accaagtcat tctgagaata gtgtatgcgg    6300
cgaccgagtt gctcttgccc ggcgtcaata cgggataata ccgcgccaca tagcagaact    6360
ttaaaagtgc tcatcattgg aaaacgttct cggggcgaa aactctcaag gatcttaccg    6420
ctgttgagat ccagttcgat gtaacccact cgtgcaccca actgatcttc agcatctttt    6480
actttcacca gcgtttctgg gtgagcaaaa acaggaaggc aaaatgccgc aaaaaaggga    6540
ataagggcga cacggaaatg ttgaatactc atactcttcc ttttt caata ttattgaagc    6600 atttatcagg gttattgtct catgagcgga tacatatttg aatgtattta gaaaaataaa    6660
caaatagggg ttccgcgcac atttccccga aaagtgccac ctgacgtc                 6708
```